US011713447B2

(12) United States Patent
Iancu-Rubin et al.

(10) Patent No.: US 11,713,447 B2
(45) Date of Patent: Aug. 1, 2023

(54) PRODUCTION OF MEGAKARYOCTYE COMPOSITIONS AND THERAPIES FOR TREATMENT OF THROMBOCYTOPENIA

(71) Applicant: Icahn School of Medicine at Mount Sinai, New York, NY (US)

(72) Inventors: Camelia Iancu-Rubin, New York, NY (US); Ronald Hoffman, New York, NY (US)

(73) Assignee: Icahn School of Medicine at Mount Sinai, New York, NY (US)

(*) Notice: Subject to any disclaimer, the term of this patent is extended or adjusted under 35 U.S.C. 154(b) by 731 days.

(21) Appl. No.: 16/322,584

(22) PCT Filed: Aug. 4, 2017

(86) PCT No.: PCT/US2017/045463
§ 371 (c)(1),
(2) Date: Feb. 1, 2019

(87) PCT Pub. No.: WO2018/027114
PCT Pub. Date: Feb. 8, 2018

(65) Prior Publication Data
US 2019/0345448 A1    Nov. 14, 2019

Related U.S. Application Data

(60) Provisional application No. 62/429,501, filed on Dec. 2, 2016, provisional application No. 62/371,024, filed on Aug. 4, 2016.

(51) Int. Cl.
*C12N 5/078*    (2010.01)
*A61K 35/19*    (2015.01)

(52) U.S. Cl.
CPC .......... *C12N 5/0644* (2013.01); *A61K 35/19* (2013.01); *C12N 2501/125* (2013.01); *C12N 2501/145* (2013.01); *C12N 2501/2303* (2013.01); *C12N 2501/2306* (2013.01); *C12N 2501/26* (2013.01); *C12N 2501/999* (2013.01); *C12N 2506/11* (2013.01)

(58) Field of Classification Search
None
See application file for complete search history.

(56) References Cited

U.S. PATENT DOCUMENTS

| 9,803,164 B2* | 10/2017 | Mitchell ............. C12N 5/0644 |
| 2014/0050711 A1 | 2/2014 | Murphy et al. |
| 2014/0205582 A1 | 7/2014 | Karsunky et al. |
| 2015/0250824 A1 | 9/2015 | Ma |
| 2016/0002586 A1 | 1/2016 | Mitchell |
| 2016/0312185 A1* | 10/2016 | Real Luna ............. C12M 23/44 |

FOREIGN PATENT DOCUMENTS

| JP | 2014-523741 A | 9/2014 |
| JP | 2015-216853 A | 12/2015 |
| WO | 2004/046312 A2 | 6/2004 |
| WO | 2008/151386 A1 | 12/2008 |
| WO | 2015/059339 A1 | 4/2015 |

OTHER PUBLICATIONS

Creating—Merriam-Webster p. 1-7; downloaded Jan. 20, 2022.*
Vulcano et al., HDAC inhibition is associated to valproic acid induction of early megakaryocytic markers Experimental Cell Research Academic Press vol. 312 No. 9 pp. 1590-1597.*
Zini et al Valproic acid triggers erythro/megakaryocyte lineage decision through induction of GFiIB and MLLT3 expression Experimental hematology Netherlands Dec. 2012 vol. 40, No. 12 pp. 1043-1054.*
Helin et al., 2013; Nature pp. 480-488 Chromatin proteins and modifications as drug targets.*
Japanese Office Action dated Jun. 28, 2021 in related Japanese Patent Application No. 2019-505379, 12 pages.
Liu B et al., "A potential activity of valproic acid in the stimulation of interleukin-3-mediated megakaryopoiesis and erythropoiesis". Experimental Hematology, vol. 38, No. 8, Aug. 2010, pp. 685-695.
Database Biosis [Online] Biosciences Information Service, Dec. 2016, Fong Helen et al., "Preclinical Development of a Cryopreservable Megakaryocyte Cell Product from Cord Blood Derived Hematopoietic Stem Cells", Database accession No. PREV201700296509, abstract, vol. 128, No. 22, p. 3859.
Database Biosis [Online] Biosciences Information Service, Dec. 2016, Iancu-Rubin Camelia et al., "Preclinical Development of a Cord Blood (CB)-Derived Hematopoietic Stem Cell (HSC) Product for Allogeneic Transplantation in Patients with Hematological Malignancies", Database accession No. PREV201700298632, abstract, vol. 128, No. 22, p. 818.
Extended European Search Report dated Mar. 20, 2020 issued in the corresponding European Patent Application No. 17837744.6.

* cited by examiner

Primary Examiner — Maria G Leavitt
(74) Attorney, Agent, or Firm — Fox Rothschild LLP

(57) ABSTRACT

The invention is directed to production of megakaryocyte (MK) compositions and their the treatment of thrombocytopenia in a subject in need thereof.

20 Claims, 26 Drawing Sheets

A

PRODUCTION OF MEGAKARYOCTYE COMPOSITIONS AND THERAPIES FOR TREATMENT OF THROMBOCYTOPENIA

I. CROSS-REFERENCE TO RELATED APPLICATIONS

The present application claims priority to U.S. Provisional Patent Application Ser. No. 62/429,501 filed Dec. 2, 2016, hereby incorporated by reference in its entirety, and to U.S. Provisional Patent Application Ser. No. 62/371,024 filed Aug. 4, 2016, hereby incorporated by reference in its entirety.

II. STATEMENT REGARDING FEDERAL FUNDING

This invention was made with government support under grant number R41HL130754 awarded by the National Institutes of Health (NIH). The U.S. Government has certain rights in this invention.

III. FIELD OF THE INVENTION

The field of the invention is production of megakaryocyte (MK) compositions and therapies for treatment of thrombocytopenia with said MK compositions.

IV. BACKGROUND

Thrombocytopenia is a rare but often serious condition characterized by a deficiency of platelets (thrombocytes) in the blood (low platelet count). Normal platelet count is between 150,000 to 450,000 platelets (PTL) per microliter (µL) of circulating blood. Thrombocytopenia occurs when the platelet count falls below normal for any reason. In rare cases, thrombocytopenia can be life-threatening, such as when platelet count falls below 10,000 PTL/µL, which may cause internal bleeding, including bleeding into the brain. The most common symptoms of thrombocytopenia include easy or excessive bruising, superficial or prolonged bleeding and/or petechiae, and in more serious cases blood in urine and/or stool, fatigue, jaundice, or an enlarged spleen. The estimated prevalence of thrombocytopenia is approximately 9.5 out of every 100,000 persons in the United States, affecting both children and adults. Thrombocytopenia often occurs as a result of a separate disorder, such as liver disease (the most common cause), immune thrombocytopenic purpura (ITP), bone marrow disorders, renal failure, pregnancy, drug-induced thrombocytopenia such as from chemotherapy, physical trauma, alcoholism and/or heavy alcohol consumption, cancers and malignancies, including leukemias, and infections, such as HIV or hepatitis C. Currently, most treatment for thrombocytopenia focuses on treating the underlying cause in hopes that the resultant low platelet count will be corrected. In serious cases, treatments may include blood or platelet transfusions. These treatments however do not provide for a solution that allows for patients to repopulate the blood with healthy and effective platelets, as the blood and platelet transfusions only provide for temporary increase in circulating platelets and rely on volunteer donors, while the focus is still on treating the underlying cause. Some experimental treatments have emerged using hematopoietic stem cell (HSC) expansion, however they have been met with limited success in regards to clinical value of the ex vivo generated product. Refractoriness to platelet transfusion and alloimmunization against human leukocyte antigen (HLA) class I antibodies is another serious clinical concern. Accordingly, there is a need for donor-independent, cell-based therapies for treatment of thrombocytopenia that allow for patients to repopulate the blood with platelet cells. Furthermore, the costs of large-scale platelet production ex vivo and the inability of platelets to tolerate long-term storage, e.g. cryopreservation, pose additional difficulties to clinical translation of culture-derived platelets. Accordingly, there is a further need for donor-independent, cell-based therapies for treatment of thrombocytopenia that allow for long-term storage of the therapeutic compositions.

V. SUMMARY OF THE INVENTION

In some embodiments, the present invention is directed to a method of generating megakaryocyte products. In some embodiments, the method comprises a first step of culturing a population of cells comprising hematopoietic stem cells (HSCs) in a first media. In some embodiments, the first media comprises at least one cytokine. In some embodiments the first media comprises at least one of stem cell factor (SCF), interleukin-3 (IL-3), Fms-like tyrosine kinase 3 (FLT-3), thrombopoietin (TPO), and combinations thereof. In some embodiments the first media comprises stem cell factor (SCF). In some embodiments the first media comprises interleukin-3 (IL-3). In some embodiments the first media comprises thrombopoietin (TPO). In some embodiments the first media does not comprise stem cell factor (SCF). In some embodiments the first media does not comprise interleukin-3 (IL-3). In some embodiments the first media does not comprise thrombopoietin (TPO). In some embodiments, the first media is serum-free (SF) media.

In some embodiments, the method comprises adding a chromatin modifying agent to the media. In some embodiments, the chromatin modifying agent comprises valproic acid (VPA). In some embodiments, the chromatin modifying agent is added about 12 hours to about 36 hours after the first step. In some embodiments, the step further comprises adding an additional cytokine. In some embodiments, the addition cytokine comprises interleukin-6 (IL-6). In some embodiments, the additional cytokine is added simultaneously with the chromatin modifying agent. In some embodiments, the additional cytokine agent is added after the chromatin modifying agent. In some embodiments, the additional cytokine agent is added before the chromatin modifying agent.

In some embodiments, the method comprises expanding the population of cells for a first time. In some embodiments, the first expanding step occurs for about 24 hours to about 120 hours. In some embodiments, the first expanding step occurs for about 24 hours to about 120 hours. In some embodiments, the first expanding step occurs for about 24 hours to about 36 hours. In some embodiments, the first expanding step occurs for about 24 hours to about 48 hours. In some embodiments, the first expanding step occurs for about 36 hours to about 48 hours. In some embodiments, the first expanding step occurs for about 24 hours to about 72 hours. In some embodiments, the first expanding step occurs for about 36 hours to about 72 hours. In some embodiments, the first expanding step occurs for about 48 hours to about 72 hours. In some embodiments, the first expanding step occurs for about 72 hours to about 96 hours. In some embodiments, the first expanding step occurs for about 72 hours to about 120 hours. In some embodiments, the first expanding step occurs for about 96 hours to about 120 hours.

In some embodiments, the first expanding step occurs for about 48 hours to about 120 hours. In some embodiments, the first expanding step occurs for about 24 hours to about 120 hours. In some embodiments, the first expanding step occurs for about 36 hours to about 96 hours. In some embodiments, the first expanding step occurs for about 48 hours to about 96 hours.

In some embodiments, the method comprises a step of culturing the population of cells on a second media. In some embodiments, the second media comprises at least one cytokine. In some embodiments the second media comprises at least one of stem cell factor (SCF), interleukin-3 (IL-3), Fms-like tyrosine kinase 3 (FLT-3), thrombopoietin (TPO), and combinations thereof. In some embodiments the second media comprises at least one of at least one of stem cell factor (SCF) and thrombopoietin (TPO). In some embodiments the second media comprises stem cell factor (SCF). In some embodiments the second media comprises interleukin-3 (IL-3). In some embodiments the second media comprises thrombopoietin (TPO). In some embodiments the second media does not comprise stem cell factor (SCF). In some embodiments the second media does not comprise interleukin-3 (IL-3). In some embodiments the second media does not comprise thrombopoietin (TPO). In some embodiments, the second media is serum-free (SF) media.

In some embodiments, the method comprises expanding the population of cells for a second time. In some embodiments, the second expanding step occurs for about 24 hours to about 120 hours. In some embodiments, the second expanding step occurs for about 24 hours to about 36 hours. In some embodiments, the second expanding step occurs for about 24 hours to about 48 hours. In some embodiments, the second expanding step occurs for about 36 hours to about 48 hours. In some embodiments, the second expanding step occurs for about 24 hours to about 72 hours. In some embodiments, the second expanding step occurs for about 36 hours to about 72 hours. In some embodiments, the second expanding step occurs for about 48 hours to about 72 hours. In some embodiments, the second expanding step occurs for about 72 hours to about 96 hours. In some embodiments, the second expanding step occurs for about 72 hours to about 120 hours. In some embodiments, the second expanding step occurs for about 96 hours to about 120 hours. In some embodiments, the second expanding step occurs for about 48 hours to about 120 hours. In some embodiments, the second expanding step occurs for about 24 hours to about 120 hours. In some embodiments, the second expanding step occurs for about 36 hours to about 96 hours. In some embodiments, the second expanding step occurs for about 48 hours to about 96 hours.

In some embodiments, the method comprises a step of culturing the population of cells on a third media. In some embodiments, the third media comprises at least one cytokine. In some embodiments the third media comprises at least one of stem cell factor (SCF), interleukin-3 (IL-3), Fms-like tyrosine kinase 3 (FLT-3), thrombopoietin (TPO), and combinations thereof. In some embodiments the third media comprises at least one of at least one of stem cell factor (SCF) and thrombopoietin (TPO). In some embodiments the third media comprises stem cell factor (SCF). In some embodiments the third media comprises interleukin-3 (IL-3). In some embodiments the third media comprises thrombopoietin (TPO). In some embodiments the third media does not comprise stem cell factor (SCF). In some embodiments the third media does not comprise interleukin-3 (IL-3). In some embodiments the third media does not comprise thrombopoietin (TPO). In some embodiments, the third media is serum-free (SF) media. In some embodiments, the culturing step comprises inducing megakaryocyte product development bias. In some embodiments, the megakaryocyte product development bias is to megakaryocyte progenitors. In some embodiments, the megakaryocyte product development bias is to immature megakaryocytes. In some embodiments, the megakaryocyte product development bias is to mature megakaryocytes.

In some embodiments, the method comprises expanding the population of cells for a third time. In some embodiments, the third expanding step occurs for about 24 hours to about 120 hours. In some embodiments, the third expanding step occurs for about 24 hours to about 120 hours. In some embodiments, the third expanding step occurs for about 24 hours to about 36 hours. In some embodiments, the third expanding step occurs for about 24 hours to about 48 hours. In some embodiments, the third expanding step occurs for about 36 hours to about 48 hours. In some embodiments, the third expanding step occurs for about 24 hours to about 72 hours. In some embodiments, the third expanding step occurs for about 36 hours to about 72 hours. In some embodiments, the third expanding step occurs for about 48 hours to about 72 hours. In some embodiments, the third expanding step occurs for about 72 hours to about 96 hours. In some embodiments, the third expanding step occurs for about 72 hours to about 120 hours. In some embodiments, the third expanding step occurs for about 96 hours to about 120 hours. In some embodiments, the third expanding step occurs for about 48 hours to about 120 hours. In some embodiments, the third expanding step occurs for about 24 hours to about 120 hours. In some embodiments, the third expanding step occurs for about 36 hours to about 96 hours. In some embodiments, the third expanding step occurs for about 48 hours to about 96 hours.

In some embodiments, the method comprises inducing megakaryocyte product development bias. In some embodiments, the megakaryocyte product development bias is to megakaryocyte progenitors. In some embodiments, the megakaryocyte product development bias is to immature megakaryocytes. In some embodiments, the megakaryocyte product development bias is to mature megakaryocytes.

In some embodiments, the method comprises a step of collecting a resultant megakaryocyte product. In some embodiments, the megakaryocyte product comprises at least one of megakaryocyte progenitors, immature megakaryocytes, mature megakaryocytes, and combinations thereof. In some embodiments, the method comprises a step of cryopreserving the resultant megakaryocyte product.

In some embodiments, the present invention is directed to megakaryocyte products. In some embodiments, the megakaryocyte products are for use in the treatment of thrombocytopenia. In some embodiments, the megakaryocyte product comprises megakaryocyte progenitors. In some embodiments, the megakaryocyte product comprises immature megakaryocytes. In some embodiments, the megakaryocyte product comprises mature megakaryocytes. In some embodiments, the megakaryocyte product comprises at least one of megakaryocyte progenitors, immature megakaryocytes, mature megakaryocytes, and combinations thereof. In some embodiments, the product is capable of undergoing cryopreservation. In some embodiments, the product is cryopreserved.

In some embodiments, the megakaryocyte products are CD41+ megakaryocyte products. In some embodiments, the composition comprises at least 5% CD41+ megakaryocyte products. In some embodiments, the composition comprises at least 10% CD41+ megakaryocyte products. In some embodiments, the composition comprises at least 15% CD41+ megakaryocyte products. In some embodiments, the composition comprises at least 20% CD41+ megakaryocyte products. In some embodiments, the composition comprises at least 25% CD41+ megakaryocyte products. In some embodiments, the composition comprises at least 30% CD41+ megakaryocyte products. In some embodiments, the composition comprises at least 35% CD41+ megakaryocyte products. In some embodiments, the composition comprises at least 40% CD41+ megakaryocyte products. In some embodiments, the composition comprises at least 45% CD41+ megakaryocyte products. In some embodiments, the composition comprises at least 50% CD41+ megakaryocyte products. In some embodiments, the composition comprises at least 55% CD41+ megakaryocyte products. In some embodiments, the composition comprises at least 60% CD41+ megakaryocyte products. In some embodiments, the composition comprises at least 65% CD41+ megakaryocyte products. In some embodiments, the composition comprises at least 70% CD41+ megakaryocyte products. In some embodiments, the composition comprises at least 75% CD41+ megakaryocyte products. In some embodiments, the composition comprises at least 80% CD41+ megakaryocyte products. In some embodiments, the composition comprises at least 85% CD41+ megakaryocyte products. In some embodiments, the composition comprises at least 90% CD41+ megakaryocyte products. In some embodiments, the composition comprises at least 95% CD41+ megakaryocyte products.

In some embodiments, the megakaryocyte progenitors are in an amount of less than 1%. In some embodiments, the megakaryocyte progenitors are in an amount of less than 2%. In some embodiments, the megakaryocyte progenitors are in an amount of less than 3%. In some embodiments, the megakaryocyte progenitors are in an amount of less than 4%. In some embodiments, the megakaryocyte progenitors are in an amount of less than 5%. In some embodiments, the megakaryocyte progenitors are in an amount of less than 6%. In some embodiments, the megakaryocyte progenitors are in an amount of less than 7%. In some embodiments, the megakaryocyte progenitors are in an amount of less than 8%. In some embodiments, the megakaryocyte progenitors are in an amount of less than 9%. In some embodiments, the megakaryocyte progenitors are in an amount of less than 10%. In some embodiments, the megakaryocyte progenitors are in an amount of less than 12%. In some embodiments, the megakaryocyte progenitors are in an amount of less than 15%. In some embodiments, the megakaryocyte progenitors are in an amount of less than 20%. In some embodiments, the megakaryocyte progenitors are in an amount from about 1% to about 5%. In some embodiments, the megakaryocyte progenitors are in an amount from about 1% to about 10%. In some embodiments, the megakaryocyte progenitors are in an amount from about 5% to about 10%. In some embodiments, the megakaryocyte progenitors are in an amount from about 1% to about 15%. In some embodiments, the megakaryocyte progenitors are in an amount from about 5% to about 15%. In some embodiments, the megakaryocyte progenitors are in an amount from about 1% to about 20%. In some embodiments, the megakaryocyte progenitors are in an amount from about 5% to about 20%. In some embodiments, the megakaryocyte progenitors are in an amount from about 10% to about 20%.

In some embodiments, the immature megakaryocytes are in an amount of less than 20%. In some embodiments, the immature megakaryocytes are in an amount of less than 25%. In some embodiments, the immature megakaryocytes are in an amount of less than 30%. In some embodiments, the immature megakaryocytes are in an amount of less than 35%. In some embodiments, the immature megakaryocytes are in an amount of less than 40%. In some embodiments, the immature megakaryocytes are in an amount of less than 45%. In some embodiments, the immature megakaryocytes are in an amount of less than 50%. In some embodiments, the immature megakaryocytes are in an amount from about 20% to about 25%. In some embodiments, the immature megakaryocytes are in an amount from about 20% to about 30%. In some embodiments, the immature megakaryocytes are in an amount from about 25% to about 30%. In some embodiments, the immature megakaryocytes are in an amount from about 25% to about 35%. In some embodiments, the immature megakaryocytes are in an amount from about 25% to about 40%. In some embodiments, the immature megakaryocytes are in an amount from about 25% to about 50%. In some embodiments, the immature megakaryocytes are in an amount from about 30% to about 50%. In some embodiments, the immature megakaryocytes are in an amount from about 35% to about 50%. In some embodiments, the immature megakaryocytes are in an amount from about 40% to about 50%. In some embodiments, the immature megakaryocytes are in an amount from about 45% to about 50%.

In some embodiments, the mature megakaryocytes are in an amount of at least 25%. In some embodiments, the mature megakaryocytes are in an amount at least 30%. In some embodiments, the mature megakaryocytes are in an amount of at least 35%. In some embodiments, the mature megakaryocytes are in an amount of at least 40%. In some embodiments, the mature megakaryocytes are in an amount of at least 45%. In some embodiments, the mature megakaryocytes are in an amount of at least 50%. In some embodiments, the mature megakaryocytes are in an amount of at least 55%. In some embodiments, the mature megakaryocytes are in an amount of at least 60%. In some embodiments, the mature megakaryocytes are in an amount of at least 65%. In some embodiments, the mature megakaryocytes are in an amount of at least 70%. In some embodiments, the mature megakaryocytes are in an amount of at least 75%. In some embodiments, the mature megakaryocytes are in an amount of greater than 75%.

In some embodiments, the mature megakaryocytes are in an amount from about 25% to about 75%. In some embodiments, the mature megakaryocytes are in an amount from about 30% to about 75%. In some embodiments, the mature megakaryocytes are in an amount from about 25% to about 75%. In some embodiments, the mature megakaryocytes are in an amount from about 30% to about 75%. In some embodiments, the mature megakaryocytes are in an amount from about 35% to about 75%. In some embodiments, the mature megakaryocytes are in an amount from about 40% to about 75%. In some embodiments, the mature megakaryocytes are in an amount from about 45% to about 75%. In some embodiments, the mature megakaryocytes are in an amount from about 50% to about 75%. In some embodiments, the mature megakaryocytes are in an amount from about 55% to about 75%. In some embodiments, the mature megakaryocytes are in an amount from about 60% to about 75%. In some embodiments, the mature megakaryocytes are in an amount from about 65% to about 75%. In some embodiments, the mature megakaryocytes are in an amount from about 70% to about 75%.

In some embodiments, the present invention is directed to a method of treating thrombocytopenia in a patient in need thereof. In some embodiments, the method of treating thrombocytopenia utilizes a megakaryocyte product of the present invention. In some embodiments, the present invention is directed to a method of increasing platelet counts in a subject in need thereof. In some embodiments, the platelet count is increased to at least 10,000 platelets per microliter of circulating blood. In some embodiments, the platelet count is increased to at least 12,000 platelets per microliter of circulating blood. In some embodiments, the platelet count is increased to at least 15,000 platelets per microliter of circulating blood. In some embodiments, the platelet count is increased to at least 25,000 platelets per microliter of circulating blood. In some embodiments, the platelet count is increased to at least 50,000 platelets per microliter of circulating blood. In some embodiments, the platelet count is increased to at least 75,000 platelets per microliter of circulating blood. In some embodiments, the platelet count is increased to at least 100,000 platelets per microliter of circulating blood. In some embodiments, the platelet count is increased to at least 125,000 platelets per microliter of circulating blood. In some embodiments, the platelet count is increased to at least 150,000 platelets per microliter of circulating blood. In some embodiments, the platelet count is increased to at least 200,000 platelets per microliter of circulating blood. In some embodiments, the platelet count is increased to at least 250,000 platelets per microliter of circulating blood. In some embodiments, the platelet count is increased to at least 300,000 platelets per microliter of circulating blood. In some embodiments, the platelet count is increased to at least 350,000 platelets per microliter of circulating blood. In some embodiments, the platelet count is increased to at least 400,000 platelets per microliter of circulating blood. In some embodiments, the platelet count is increased to at least 450,000 platelets per microliter of circulating blood. In some embodiments, the present invention is directed to the use of megakaryocyte products of the invention in the manufacture of a medicament for treatment of thrombocytopenia.

VI. BRIEF DESCRIPTION OF THE DRAWINGS

FIGS. 1A and 1B represent the effect of valproic acid (VPA), a chromatin modifying agent, on the ex vivo expansion of CB CD34+ cells. FIG. 1A: CB CD34+ cells were cultured in serum-containing (SC) or serum-free (SF) media supplemented with SCF, FLT-3, IL-3, and TPO in the absence (C) or presence of VPA. More CD34+ cells and CD34+/CD90+ cells were generated in SF than in SC cultures. FIG. 1B: Phenotypic analysis of unmanipulated primary CB CD34+ cells (PC) and of CD34+ cells expanded for 7 days in SF media supplemented with SCF, FLT-3, IL-3, and TPO in the absence (Control) or presence of VPA.

FIGS. 2A, 2B, and 2C represent ex vivo megakaryocyte (MK) and platelet (PTL) generation by CB CD34+ cells. FIG. 2A: Time course analyses of MK cultures indicate a gradual decline in CD34 (diamond) expression which is accompanied by an increase in MK-specific surface markers CD41 (square)/CD42 (triangle) expression. FIG. 2B: Flow cytometric dot plot analyses of MK cultures on days 7 and 10. FIG. 2C: Flow cytometric analysis of culture-derived PTL identified by forward (FSC) and side (SSC) scatter properties (upper panel) and by dual CD41/tiazole orange staining. Freshly isolated PB PTLs were used as control.

FIGS. 3A and 3B represent the effect of valproic acid (VPA) expansion on CB CD34+ cells' ability to generate megakaryocytes (MK). FIG. 3A: Phenotypic analysis of CD41 expression MK cultures generated from CB CD34+ cells expanded with 1 mM VPA for 7 days followed by TPO-mediated MK differentiation for 7 additional days. FIG. 3B: q-PCR analyses of NF-E2, PF4 and GATA-1 expression by MK cultures generated from CD34+ cells untreated or expanded with 0.5 or 1 mM VPA.

FIG. 4 represents ex vivo generation of megakaryocytes (MKs) from valproic acid (VPA)-expanded cord blood (CB) CD34+ cells.

FIGS. 5A and 5B indicate that a robust number of CFU-MKs were formed according to the protocols set forth in Example 4. The first column of each of FIG. 5A and FIG. 5B correspond to Treatment 1, the second column corresponds to Treatment 2, the third column corresponds to Treatment 3, and the fourth column corresponds to Treatment 4.

FIGS. 6A and 6B represent that megakaryocytes (MKs) isolated from valproic acid (VPA)-expanded cultures are amenable to cryopreservation. FIG. 6A represents $CD61^+$ MK phenotype prior to cryopreservation; FIG. 6B represents $CD61^+$ MK phenotype post cryopreservation FIGS. 7A and 7B represent that cryopreserved MK generated from HSC expanded in the presence of cytokines alone or cytokines plus VPA were thawed and evaluated for their ability to release platelets ex vivo and to form CFU-MK. FIG. 7A represents flow cytometry, while FIG. 7B represents thiazole staining, with arrows pointing out platelet-forming MKs.

FIGS. 8A, 8B, 8C, 8D, 8E and 8F represent the evaluation of hPTL and hMK engraftment in vivo in NSG mice after infusion of ex vivo generated MK. FIG. 8A represents a gating strategy and evaluation of hPTL in the mPB; hPTL-rich plasma was injected in sub-lethally irradiated NSG mice and the presence of hPTL in the mPB was evaluated after 1 hour, 48 hours, and 120 hours. hPTL were gated based on size and light scatter properties and are represented as the cluster of circled dots expressing human CD41 on the dot plot histograms. FIG. 8B represents that MK cultures generated ex vivo were collected, quantified, and immunophenotypically characterized (left side dot plot histograms). 1 million TNCs comprising 0.5 million CD41+ MK were infused into sub-lethally irradiated NSG mice and the presence of hPTL produced in vivo was evaluated over a 60 day time period. Dot plot histograms on the show hPTL expressing hCD41 (upper left quadrant) and hCD42b (upper right quadrant) detected in the mPB at 3, 10, 28, and 48 days post-infusion. mPTL labeled with mouse anti-CD41 antibodies are represented in the lower right quadrant. FIG. 8C represents the kinetics and quantification of hPTL in the mPB after infusion of ex vivo generated MK cultures described in FIG. 8B. Each line represents one animal (n=7). FIG. 8D represents hPTL production in NSG mice infused with $0.25 \times 10^6$ un-manipulated CD34+ HSC and the progeny of an equivalent number of HSC expanded with cytokines plus VPA for 4 days (CC #16); the presence of hPTL in the mBP (right panel) and hMK in the mBM (left panel) were evaluated 15 weeks post-infusion. FIG. 8E represents that heterogeneous MK cultures generated after 10 days (4 days expansion with VPA followed by 6 days MK differentiation, (CC #16), were transplanted into NSG at an amount of approximately $5 \times 10^6$ per mouse; human MK engraftment in the mouse spleen (SP) and BM were evaluated 6 weeks post-transplantation, Whole mBM cells from the recipient mice were plated in semisolid media in conditions permissive for human colony formation (CFU). Human MK within CFUs formed were detected by flow cytometry and microscopic analyses using anti-human CD41 antibodies. FIG. 8F represents that 0.2 million cryopreserved purified MK generated in cultures expanded in the presence of VPA were infused into sub-lethally irradiated NSH mice and the presence of hPTL in the mPB was evaluated during a 28-day time period. Each line represents hPTL number over time in one animal (n=4).

VII. DETAILED DESCRIPTION

Figure 1:
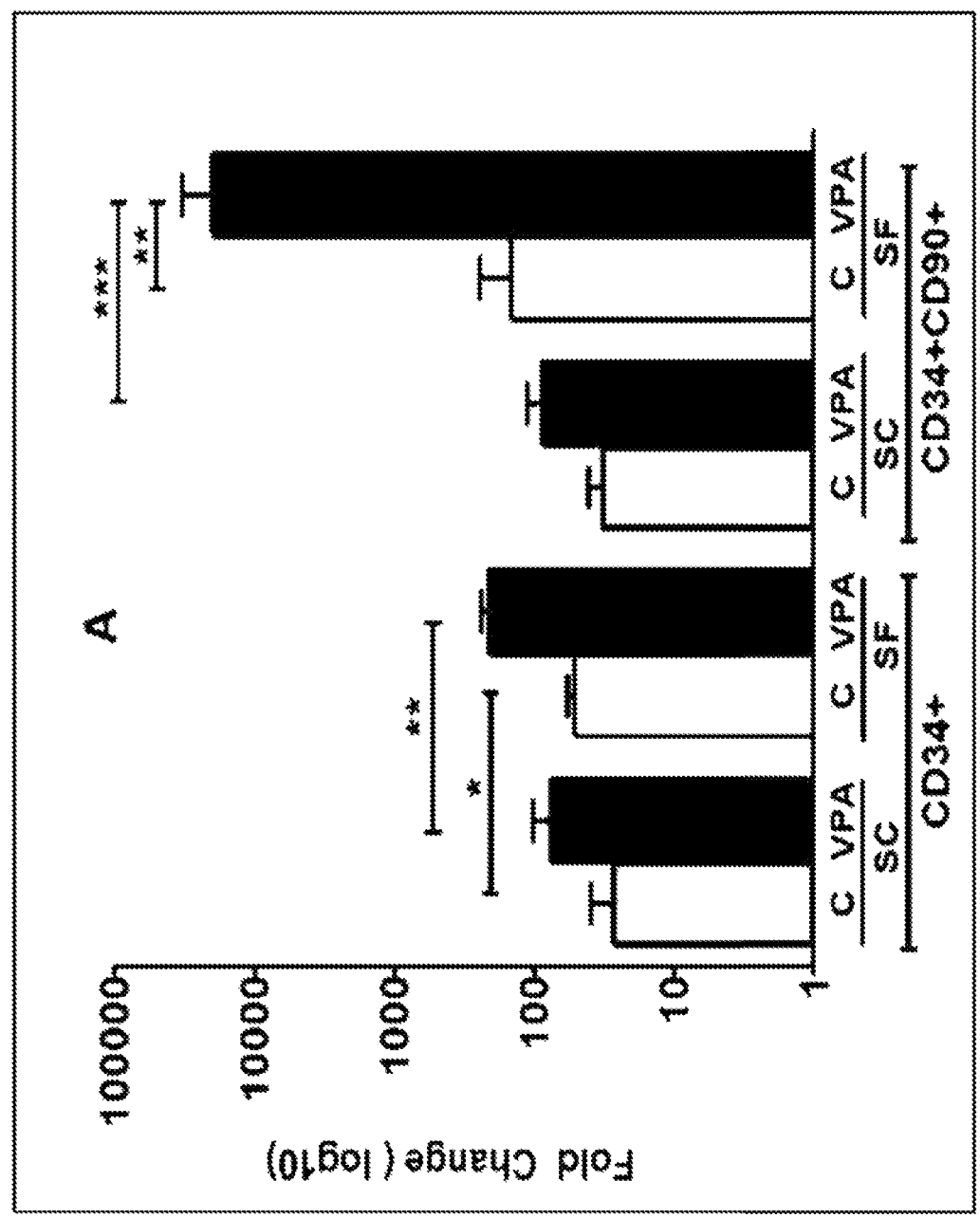
Figure 1:
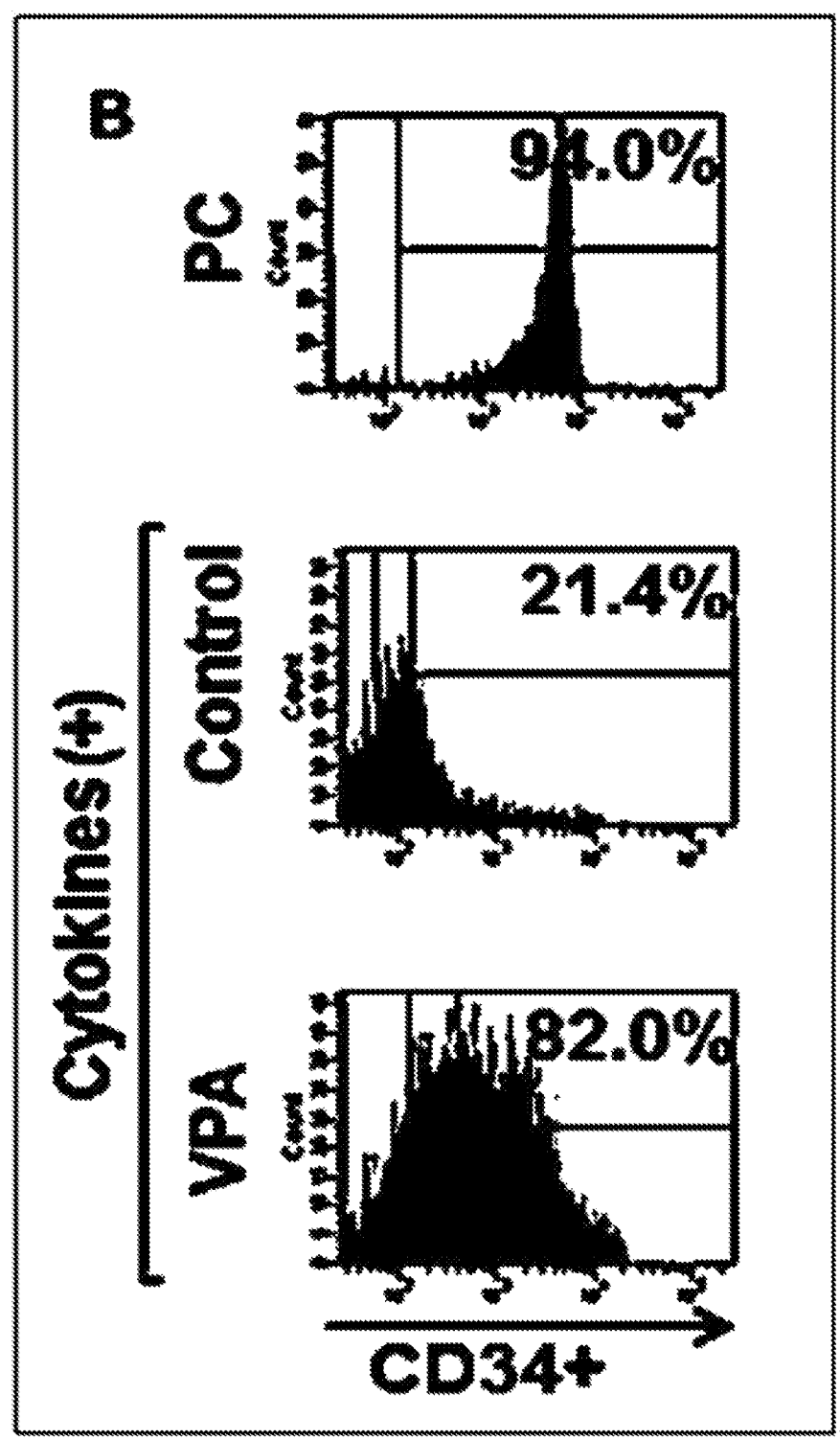

Platelet production, or thrombopoiesis, is the culmination of a unique process in which bone marrow (BM) hematopoietic stem cells (HSC)s give rise to megakaryocyte (MK) progenitors, which initially proliferate and acquire lineage-specific markers, then become polyploid megakaryocytes (i.e., duplication of the chromosome complement beyond the diploid 2N). The cells undergo further cytoplasmic maturation and pro-platelet extension, which eventually shed platelets into circulation. This release of platelets in vivo is a highly efficient event relying on both intrinsic (e.g., cytoskeletal changes) and extrinsic factors (e.g., cell-cell contact, soluble factors, and shear stress) within the bone marrow microenvironment. This highly complex process is extremely difficult to replicate ex vivo, which is a major hurdle in making clinically viable platelets ex vivo, e.g. in tissue culture flasks. Without wishing to be bound by theory, the difficulty in accurately replicating this differentiation process is why previous treatments using ex vivo hematopoietic stem cell expansion has been met with limited success. Only a very small fraction of megakaryocytes are capable of shedding platelets in vitro, with the number of platelets being produced by cultured megakaryocytes never matching the in vivo rate. Furthermore, the production of platelets ex vivo is a generally cost-prohibitive measure, and platelets do not store well under long-term storage conditions, e.g. cryopreservation.

As used herein, the term "megakaryocytes", "MK" or "MKs" refers to bone marrow cells responsible for the production of thrombocytes (platelets). The term megakaryocytes as used herein may refer to any of megakaryocyte progenitors, immature megakaryocytes, and/or mature megakaryocytes. The process by which hematopoietic stem cells (HSC) become mature megakaryocytes is known as megakaryopoesis, and generally follows the following progression. HSCs are CD34+, and are found in bone marrow (BM), peripheral blood (PB), and cord blood (CB). As shown throughout the Examples, cord blood is a preferred source of HSCs. The HSCs differentiate into megakaryocyte progenitor cells. As used herein, the term "megakaryocyte progenitors" or "MK progenitors" may refer to polyploid, typically 4N, megakaryocyte cells that are characterized as CD34+/CD41+/CD42−. The megakaryocyte progenitors then differentiate into immature megakaryocyte cells. As used herein, the term "immature megakaryocytes" or "immature MK" or "immature MKs" may refer to polyploid, typically 8N, megakaryocyte cells that are characterized as CD34−/CD41+/CD42−. The immature megakaryocyte cells then differentiate into mature megakaryocyte cells. As used herein, the term "mature megakaryocytes" or "mature MK" or "mature MKs" may refer to polyploid megakaryocytes, typically 16N, characterized by CD34−/CD41+/CD42−. The mature megakaryocyte cells are capable of platelet production in vitro, ex vivo, or in vivo.

As used herein, the term "megakaryocyte products" or "MK products" may refer to compositions that include one or more of MK progenitors, immature MKs, and/or mature MKs in different amounts. The megakaryocyte products of the present invention may be administered to a patient in need thereof to treat thrombocytopenia. The proportion of MK progenitors, immature MKs, and/or mature MKs in the megakaryocyte product compositions may be adjusted depending on the therapeutic use desired, as discussed infra. Furthermore, the megakaryocyte products of the present invention may be amenable to cryopreservation for long-term storage and thawing.

The term "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing as well as after their appearance. Thus, "treating" or "treatment" includes "preventing" or "prevention" of disease. The terms "prevent" or "preventing" refer to prophylactic and/or preventative measures, wherein the object is to prevent or slow down the targeted pathologic condition or disorder. For example, in the case of thrombocytopenia, "preventing" or "preventing" may arise in a situation where a course of treatment is advanced in order to prevent platelet count from falling below a designation threshold, for example but not necessarily, below 150,000 platelets per microliter of blood, or below 10,000 platelets per microliter of blood. In addition, "treating" or "treatment" does not require complete alleviation of signs or symptoms, does not require a cure, and specifically includes protocols that have only a marginal effect on the patient.

As used herein, the term "carriers" may include pharmaceutically acceptable carriers, excipients, or stabilizers that are nontoxic to the cell or mammal being exposed thereto at the dosages and concentrations employed. Often the pharmaceutically acceptable carrier is an aqueous pH buffered solution. Examples of physiologically acceptable carriers include, but not limited to, buffers such as phosphate, citrate, and other organic acids; antioxidants including, but not limited to, ascorbic acid; low molecular weight (less than about 10 residues) polypeptide; proteins, such as, but not limited to, serum albumin, gelatin, or immunoglobulins; hydrophilic polymers such as, but not limited to, polyvinylpyrrolidone; amino acids such as, but not limited to, glycine, glutamine, asparagine, arginine or lysine; monosaccharides, disaccharides, and other carbohydrates including, but not limited to, glucose, mannose, or dextrins; chelating agents such as, but not limited to, EDTA; sugar alcohols such as, but not limited to, mannitol or sorbitol; salt-forming counterions such as, but not limited to, sodium; and/or nonionic surfactants such as, but not limited to, TWEEN; polyethylene glycol (PEG), and PLURONICS. Any combination of such components, including probable inclusion of a bacteriostat, may be useful to fill the compositions of the present invention.

The term "patient" as used herein may refer to a biological system to which a treatment can be administered. A biological system can include, for example, an individual cell, a set of cells (e.g., a cell culture), an organ, a tissue, or a multi-cellular organism. A "patient" can refer to a human patient or a non-human patient.

The terms "effective amount" or "therapeutically effective amount" as used herein may refer to an amount of the compound or agent that is capable of producing a medically desirable result in a treated subject. The treatment method can be performed in vivo or ex vivo, alone or in conjunction with other drugs or therapy. A therapeutically effective amount can be administered in one or more administrations, applications or dosages and is not intended to be limited to a particular formulation or administration route.

The terms "co-administration," "co-administered," and "in combination with" as used herein may refer to the administration of at least two agents or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary.

The present invention uses a wide number of experimental conditions to generate the megakaryocyte products of the present invention, e.g. as shown throughout Examples 1 through 7, 9-10 and culture conditions 1 through 20 described therein (i.e. CC #1 through CC #20). The precursor products are generally CD34+ cells, e.g. cord blood (CB) CD34+ cells or peripheral blood (PB) CD34+ cells. Cord blood cells are a preferred source of CD34+ cells but the invention is not limited as such. Such methods preferably utilizes a two-step culture system of defined MK populations: CD34+/CD41+/CD42b− MK precursors (MKP), immature CD34−/CD41+/CD42b− MK (iMK), and mature CD34−/CD41+/CD42b+ MK (mMK). The yield obtained in these cultures is robust, however it can be restricted due to the numbers of CD34+ cells in, for example, cord blood. The numbers of CD34+ cells can be greatly expanded by epigenetic reprogramming following treatment with a chromatin modifying agent, for example, valproic acid (VPA) used in the Examples. The integration and optimization of hematopoietic stem cells (HSCs) with MK differentiation is disclosed herein, which results in the generation of a clinically relevant MK cell product. The Examples disclose 20 different culture conditions, labeled CC #1 through CC #20, in which CD34+ cells were cultured for a first period of time (e.g. 5 to 8 days) in the absence or presence of VPA in serum-free media with various cytokines in order to allow for HSC expansion. The resulting HSC pool was cultured for an additional second period of time (e.g. 4 to 7 days) in MK differentiation/maturation media. The overall observed yield ranged from 8 to 33 MK per input CD34+ cell expanded in the presence of cytokines alone (see, e.g, TABLE 4, Example 9 infra), and from 9 to 34 MK per input CD34+ cell expanded in the presence of cytokines plus VPA. Without wishing to be bound by theory, given that up to $2 \times 10^6$ CD34+ cells can be isolated from a single CBU, a culture yielding 28 or more MK per one CD34+ cell is capable of generating over $56 \times 10^6$ MK or the equivalent of $7 \times 10^5$ CD41+ MK/kg/body weight for infusion into a normal adult of about 80 kg, a surprisingly high and clinically relevant yield.

In greater detail, the methods generally comprise the following. First, CD34+ cells are obtained. Once the CD34+ cells are obtained, they are subjected to a cytokine priming in media. The media is preferably serum-free (SF) media. The cytokine priming may, but not necessarily includes stem cell factor (SCF), interleukin-3 (IL-3), thrombopoietin (TPO), and/or Fms-like tyrosine kinase 3 (FLT-3). The SCF may be in an amount from about 1 ng/mL to about 250 ng/mL, including any intervening ranges, e.g. about 150 ng/mL. The IL-3 may be in an amount from about 1 ng/mL to about 100 ng/mL, including any intervening ranges, e.g. about 50 ng/mL. The TPO may be in an amount from about 1 ng/mL to about 200 ng/mL, including any intervening ranges, e.g. about 100 ng/mL. The FLT-3 may be in an amount from about 1 ng/mL to about 200 ng/mL, including any intervening ranges, e.g. about 100 ng/mL. While the cytokine priming typically includes each of these listed agents, not all necessarily needs to be present.

After cytokine priming has occurred, the cells may or may not be exposed to a chromatin modifying agent. A review of chromatin modifying agents can be found in Seidel et al., Chromatin-modifying agents in anti-cancer therapy, *Biochimie* 94(11):2264-79. An exemplary chromatin-modifying agent is valproic acid (VPA). The chromatin modifying agent is typically added about 1 day, i.e. about 24 hours after the cytokine priming, although it may be added with the cytokine priming up through about 3 days, i.e. about 72 hours after the cytokine priming, including any intervening ranges. The chromatin modifying agent is generally added in an amount from about 0.1 mM to about 5 mM, including any intervening ranges, e.g. about 1 mM. Additional cytokines may be added alongside the chromatin modifying agent or afterwards, e.g. within 24-48 hours after addition of the chromatin modifying agent, including, but not limited to, interleukin-6 (IL-6). Alternatively, IL-6 may be added to the original cytokine priming. IL-6 may be added in an amount from about 5 ng/mL to about 100 ng/mL, including any intervening ranges, e.g. about 50 ng/mL.

After addition of the optional chromatin modifying agent and any additional cytokines, the cell culture is allowed to expand for about 1 day to about 5 days, i.e. about 24 hours to about 120 hours, including any intervening ranges. After this first expansion, the cells are optionally re-plated into a second media. The second media is preferably serum-free (SF) media. Additional cytokines may be present in the second media, including but not limited to, SCF and TPO, e.g. in an amount from about 1 ng/mL to about 250 ng/mL, including any intervening ranges, e.g. about 100 or 150 ng/mL. The second media is ideally free of chromatin modifying agents such as VPA. The cell culture is allowed to undergo a second expansion for about 1 day to about 5 days, i.e. about 24 hours to about 96 hours, including any intervening ranges. After this second expansion, the cells are optionally re-plated onto a third media. The third media is preferably serum-free (SF) media. The third media may have TPO in an amount from about 1 ng/mL to about 200 ng/mL, including any intervening ranges, e.g. about 100 ng/mL. The third media is ideally free of SCF and any chromatin modifying agents such as VPA. The cell culture may be allowed to undergo a third expansion for about 1 day to about 5 days, i.e. about 24 hours to about 120 hours, including any intervening ranges, but is more preferably about 72 hours to about 120 hours. After this third expansion, the cells are collected.

The megakaryocyte products of the present invention, as shown in Example 6 infra, are surprisingly capable of undergoing cryopreservation for long-term storage, with a high percentage of megakaryocyte products alive after thawing. Viability of cryopreserved MK cultures post-thaw was 71% on average with no changes in the MK phenotype. Thrombocytes (platelets) do not survive cryopreservation, so the fact that the megakaryocyte products of the present invention are capable of surviving cryopreservation is significant because it solves a fundamental problem with platelet transfusion and storage. The megakaryocyte products of the present invention that are suitable for cryopreservation may comprise a mixture of MK progenitors, immature MKs, and/or mature MKs. An exemplary embodiment of a megakaryocyte product that is amenable to cryopreservation is less than about 1% to about 5% MK progenitor, about 25% to about 35% immature MK, and about 55% to about 75% mature MKs. However, the exact range of individual types of megakaryocytes in the megakaryocyte products may be variable. For example, the amount of MK progenitor may be less than 1%, about 1%, about 2%, about 3%, about 4%, about 5%, about 6%, about 7%, about 8%, about 9%, about 10%, about 12%, about 15%, about 20%, about 25%, about 30%, about 35%, about 40%, about 45%, about 50%, about 55%, about 60%, about 65%, about 70%, about 75%, about 80%, about 85%, about 90%, about 95%, about 98%, about 99%, greater than 99%, and any intervening ranges therein, the amount of immature MK may be less than 1%, about 1%, about 2%, about 3%, about 4%, about 5%, about 6%, about 7%, about 8%, about 9%, about 10%, about 12%, about 15%, about 20%, about 25%, about 30%, about 35%, about 40%, about 45%, about 50%, about 55%, about 60%, about 65%, about 70%, about 75%, about 80%, about 85%, about 90%, about 95%, about 98%, about 99%, greater than 99%, and any intervening ranges therein, and the amount of mature MK may be less than 1%, about 1%, about 2%, about 3%, about 4%, about 5%, about 6%, about 7%, about 8%, about 9%, about 10%, about 12%, about 15%, about 20%, about 25%, about 30%, about 35%, about 40%, about 45%, about 50%, about 55%, about 60%, about 65%, about 70%, about 75%, about 80%, about 85%, about 90%, about 95%, about 98%, about 99%, greater than 99%, and any intervening ranges therein. The megakaryocyte product may contain pharmaceutically acceptable carriers, preservatives, or other compositions that don't adversely affect the megakaryocytes contained therein.

In some embodiments, the present invention comprises a method of administering a therapeutically effective amount of a megakaryocyte product to a patient in need thereof in order to treat thrombocytopenia. The megakaryocyte product can include megakaryocyte precursors, immature megakaryocytes, mature megakaryocytes, and combinations thereof. Each of these particular megakaryocyte groups will generate platelets in patients at different time points and as such may possess different therapeutic utility. For example, mature megakaryocytes will produce platelets within days of being administered to the patient, whereas immature megakaryocytes will produce platelets within weeks, and megakaryocyte precursors will produce platelets within months. Thus, depending on the need of the patients, the treatment can be optimized to include one or more types of megakaryocytes in the megakaryocyte product.

The megakaryocyte products of the present invention, either alone or in combination, may be used in vivo. In accordance, the present invention provides for administering a pharmaceutical composition comprising a pharmaceutically acceptable carrier and a pharmacologically effective amount of one or more of the subject peptides, or suitable salts thereof. The pharmaceutical composition may be formulated as powders, granules, solutions, suspensions, aerosols, solids, pills, tablets, capsules, gels, topical crèmes, suppositories, transdermal patches, etc.

The megakaryocyte product may be administered intravenously. Intravenous delivery of megakaryocyte products may include any formulation suitable for administration to a patient via any intravenous method, including a bolus. The megakaryocyte product may be administered to a patient via an injection method. Suitable injection methods may include, in addition to intravenous injection, intra-arterial infusion, intramuscular injection, transdermal injection, parentally, and subcutaneous injection. The megakaryocyte formulation may include an aqueous vehicle. Aqueous vehicles include, by way of example and without limitation, sodium chloride, calcium chloride, ringer's solution, isotonic dextrose solution, sterile water, dextrose, and lactated ringers solution. Nonaqueous parenteral vehicles include, by way of example and without limitation, fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p hydroxybenzoic acid esters, thimerosal, benzalkonium chloride and benzethonium chloride. Isotonic agents include, by way of example and without limitation, sodium chloride and dextrose. Buffers may include phosphate and citrate. Antioxidants may include sodium bisulfate.

The dose and dosage regimen depends upon a variety of factors readily determined by a physician, such as the nature of the disorder, for example, its therapeutic index, the patient, and the patient's history. Generally, a therapeutically effective amount of a composition is administered to a patient. In some embodiments, the amount of composition administered is in the range of about 0.01 mg/kg to about 1000 mg/kg of patient body weight, and any range in between. Depending on the severity of condition, about 0.1 mg/kg to about 50 mg/kg body weight (for example, about 0.1-15 mg/kg/dose, more usually from about 1-25 mg/kg body weight) of composition is an initial candidate dosage for administration to the patient, whether, for example, by one or more separate administrations, or by continuous infusion. The compositions may be delivered relatively low volume rates, for example but not necessarily from about 0.001 ml/day to 10 ml/day so as to minimize tissue disturbance or trauma near the site where the formulation is released. The formulation may be released at a rate of, depending on the specific biological agent(s), at a low dose, e.g., from about 0.01 µg/hr or 0.1 µg/hr, 0.25 µg/hr, 1 µg/hr, generally up to about 200 µg/hr, or the formulation is delivered at a low volume rate e.g., a volume rate of from about 0.001 ml/day to about 1 ml/day, for example, 0.01 micrograms per day up to about 20 milligrams per day. Dosage depends on a number of factors such as potency, bioavailability, and toxicity of the active ingredient and the requirements of the subject. The progress of this therapy is readily monitored by conventional methods and assays and based on criteria known to the physician or other persons of skill in the art. The above parameters for assessing successful treatment and improvement in the disease are readily measurable by routine procedures familiar to a physician.

The delivery systems also include sustained release or long term delivery methods, which are well known to those skilled in the art. By "sustained release or" "long term release" as used herein is meant that the delivery system administers a pharmaceutically therapeutic amount of subject compounds for more than a day, preferably more than a week, and most preferable at least about 30 days to 60 days, or longer. Long term release systems may comprise implantable solids or gels containing the subject peptide, such as biodegradable polymers described above; pumps, including peristaltic pumps and fluorocarbon propellant pumps; osmotic and mini-osmotic pumps; and the like. Peristaltic pumps deliver a set amount of drug with each activation of the pump, and the reservoir can be refilled, preferably percutaneously through a port. A controller sets the dosage and can also provide a readout on dosage delivered, dosage remaining, and frequency of delivery. Fluorocarbon propellant pumps utilize a fluorocarbon liquid to operate the pump. The fluorocarbon liquid exerts a vapor pressure above atmospheric pressure and compresses a chamber containing the drug to release the drug. Osmotic pumps (and mini-osmotic pumps) utilize osmotic pressure to release the drug at a constant rate. The drug is contained in an impermeable diaphragm, which is surrounded by the osmotic agent. A semipermeable membrane contains the osmotic agent, and the entire pump is housed in a casing. Diffusion of water through the semipermeable membrane squeezes the diaphragm holding the drug, forcing the drug into bloodstream, organ, or tissue. These and other such implants are particularly useful in treating an inflammatory disease condition, especially those manifesting recurring episodes or which are progressive in nature, by delivering the oligopeptides of the invention via systemic (e.g., intravenous or subcutaneous) or localized doses in a sustained, long term manner.

Where a value of ranges is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference in their entireties.

As used herein and in the appended claims, the singular forms "a", "and" and "the" include plural references unless the context clearly dictates otherwise.

The term "about" refers to a range of values which would not be considered by a person of ordinary skill in the art as substantially different from the baseline values. For example, the term "about" may refer to a value that is within 20%, 15%, 10%, 9%, 8%, 7%, 6%, 5%, 4%, 3%, 2%, 1%, 0.5%, 0.1%, 0.05%, or 0.01% of the stated value, as well as values intervening such stated values.

Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates which may need to be independently confirmed.

Each of the applications and patents cited in this text, as well as each document or reference, patent or non-patent literature, cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference in their entirety. More generally, documents or references are cited in this text, either in a Reference List before the claims; or in the text itself; and, each of these documents or references ("herein-cited references"), as well as each document or reference cited in each of the herein-cited references (including any manufacturer's specifications, instructions, etc.), is hereby expressly incorporated herein by reference.

The following non-limiting examples serve to further illustrate the present invention.

VIII. EXAMPLES

The following examples relate to in vitro expansion and differentiation of cord blood (CB) CD34+ cells into megakaryocytes (MKs), the cryopreservation of the resultant MK products, as well as in vivo transfusion of MK products generated via expansion/differentiation. Where cell culture conditions are listed, an accompanying identifier, e.g. CC #1, is provided, which corresponds to TABLE 5, infra. The overall yield of CD41$^+$ MKs obtained from different cell culture conditions listed throughout the Examples ranged from 8-33 MK per input CD34$^+$ cell expanded in the presence of cytokines alone and from 9-34 MK per input CD34$^+$ cell expanded in the presence of cytokines plus VPA. Given that up to $2\times10^6$ CD34$^+$ cells can be isolated from one CBU, while not wishing to be bound by theory, a culture yielding 28 or more MK/input CD34$^+$ cell is expected to generate over $56\times10^6$ MK or the equivalent of $7\times10^5$ MK/kg for infusion into an 80 kg recipient.

1. Expansion of CD34+ Cells in Serum-Free (SF) Cultures by Valproic Acid (VPA) Treatment Cord blood (CB) CD34+ cells were obtained and separated into a testing group and a control group. The groups were subjected to the following cell culture protocol:

Day 0:

The CB CD34+ cells were primed with a cytokine cocktail and plated in serum-free (SF) culture. The cytokine cocktail included stem cell factor (SCF) at an amount of 150 ng/mL, interleukin-3 (IL-3) at an amount of 50 ng/mL, Fms-like tyrosine kinase 3 (FLT-3) at an amount of 100 ng/mL, and thrombopoietin (TPO) at an amount of 100 ng/mL.

Day 1:

1 mM valproic acid (VPA) was added to the SF culture (testing group only). No VPA was added to the control group.

Days 2-8:

The cells were allowed to expand in the SF culture and collected at Day 7. Total CD34+ cell expansion was around 200-fold.

The results indicated that the number of CD34+ cells in VPA-treated cultures (testing groups) was >200-fold greater than the number of cells expanded in the absence of VPA, see FIG. 1. The expanded HSCs consisted predominantly of primitive CD34+/CD90+ cells (74.2±9.8%), followed by glycophorin (GPA)+erythroid cells (17±5.4%), and CD41+ MK cells (8.9±2%). In vitro and in vivo evaluation of VPA-expanded CD34+ cells' function demonstrated an increased ability to reconstitute multilineage hematopoiesis following transplantation in NSG mice, including improved MK lineage engraftment.

2. Megakaryocytes (MKs) at Different Developmental Stages are Efficiently Generated Ex Vivo from Primary CD34+ Cells Cord blood (CB) CD34+ cells were obtained. The groups were subjected to the following cell culture protocol.

Day 0:

The CD34+ cells were plated on stem cell factor (SCF) media with thrombopoietin (TPO).

Days 1-7:

The cells grew in culture.

Day 7:

The cells were re-plated with serum-free (SF) culture with thrombopoietin (TPO)

Days 8-14:

The cells were allowed to differentiate into megakaryocyte production.

Day 14:

The cells were collected, quantified and characterized. Total CD41+ megakaryocyte expansion was around 3 to 15-fold.

Figure 2:
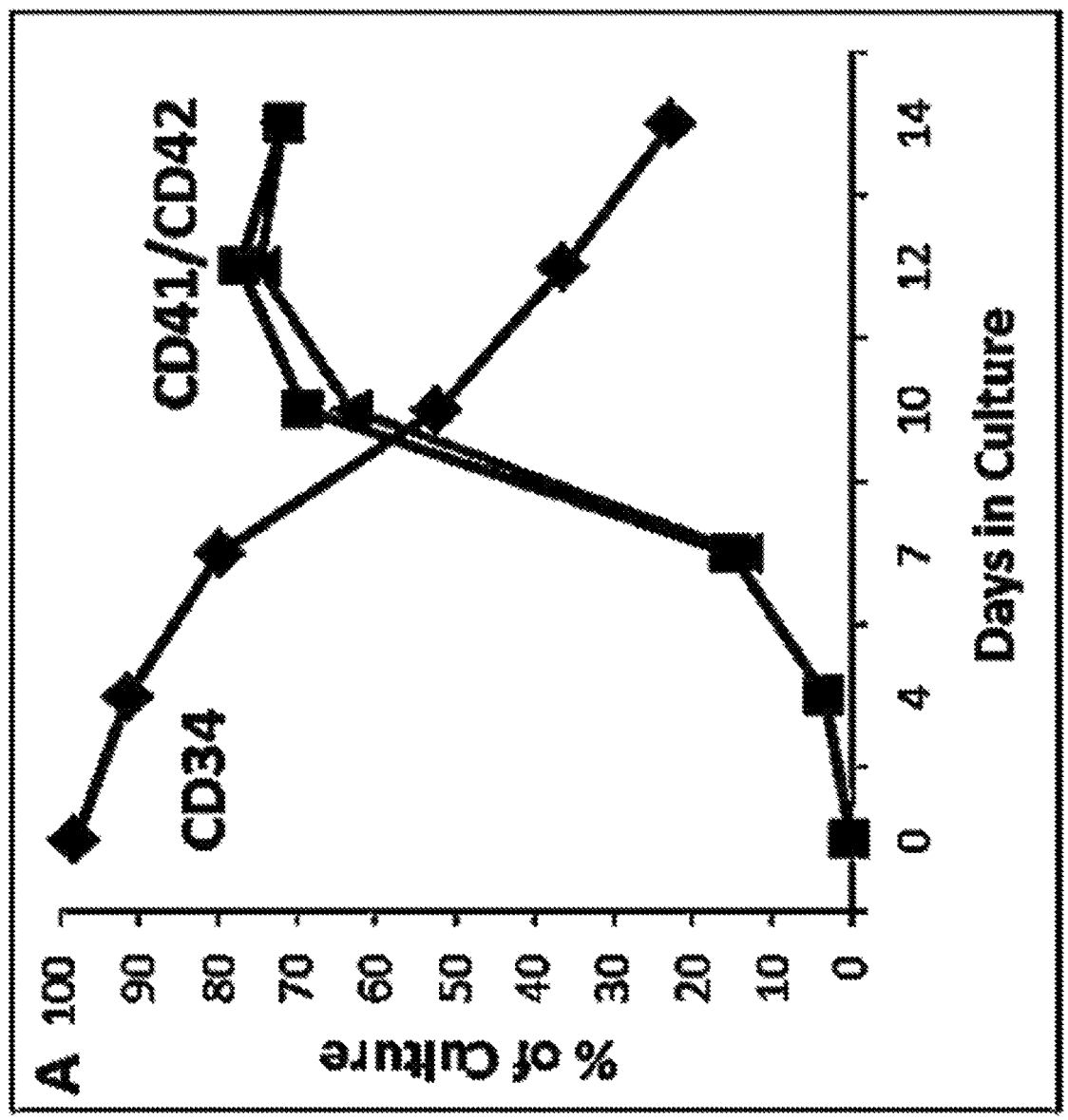
Figure 2:
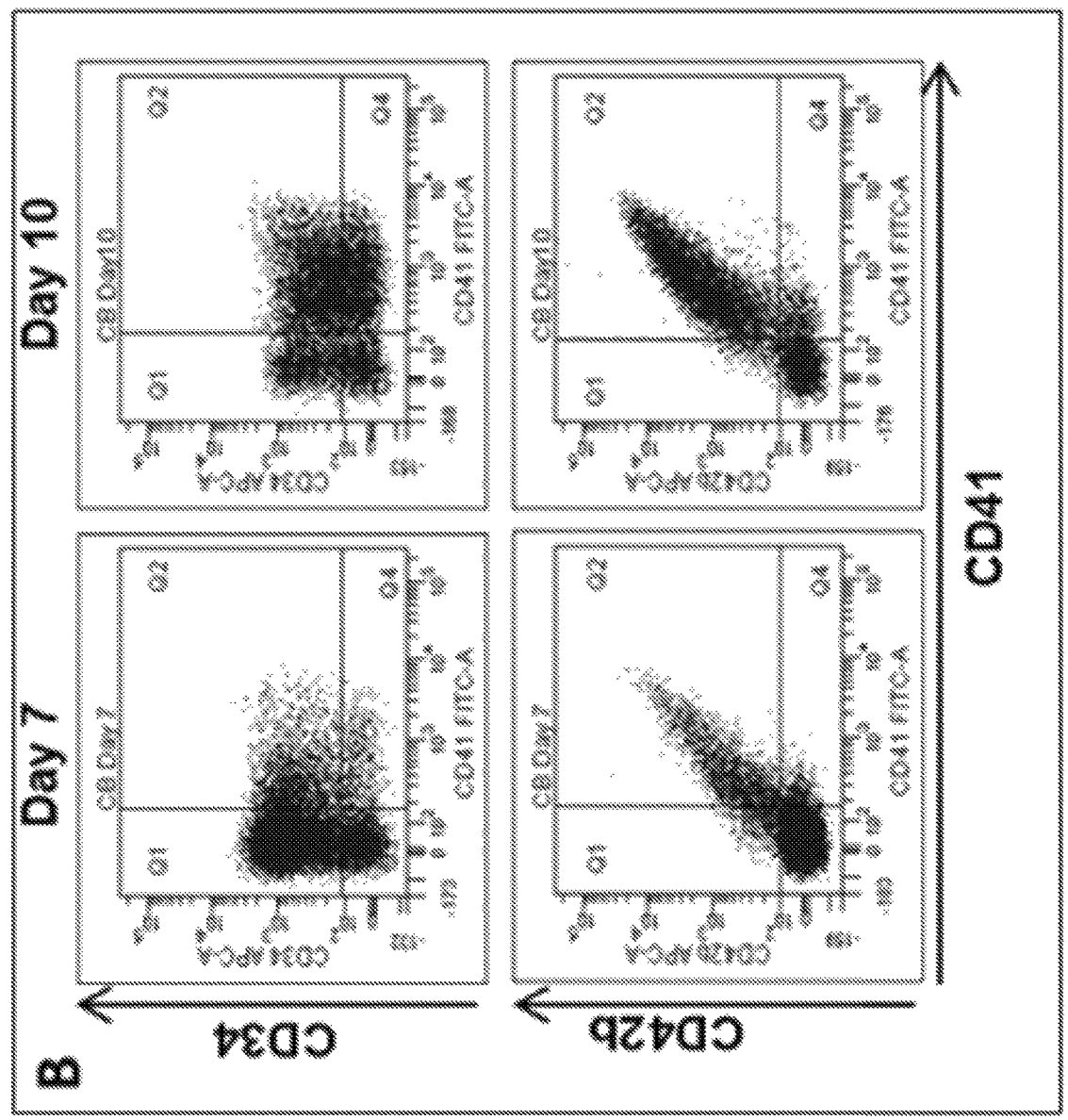
Figure 2:
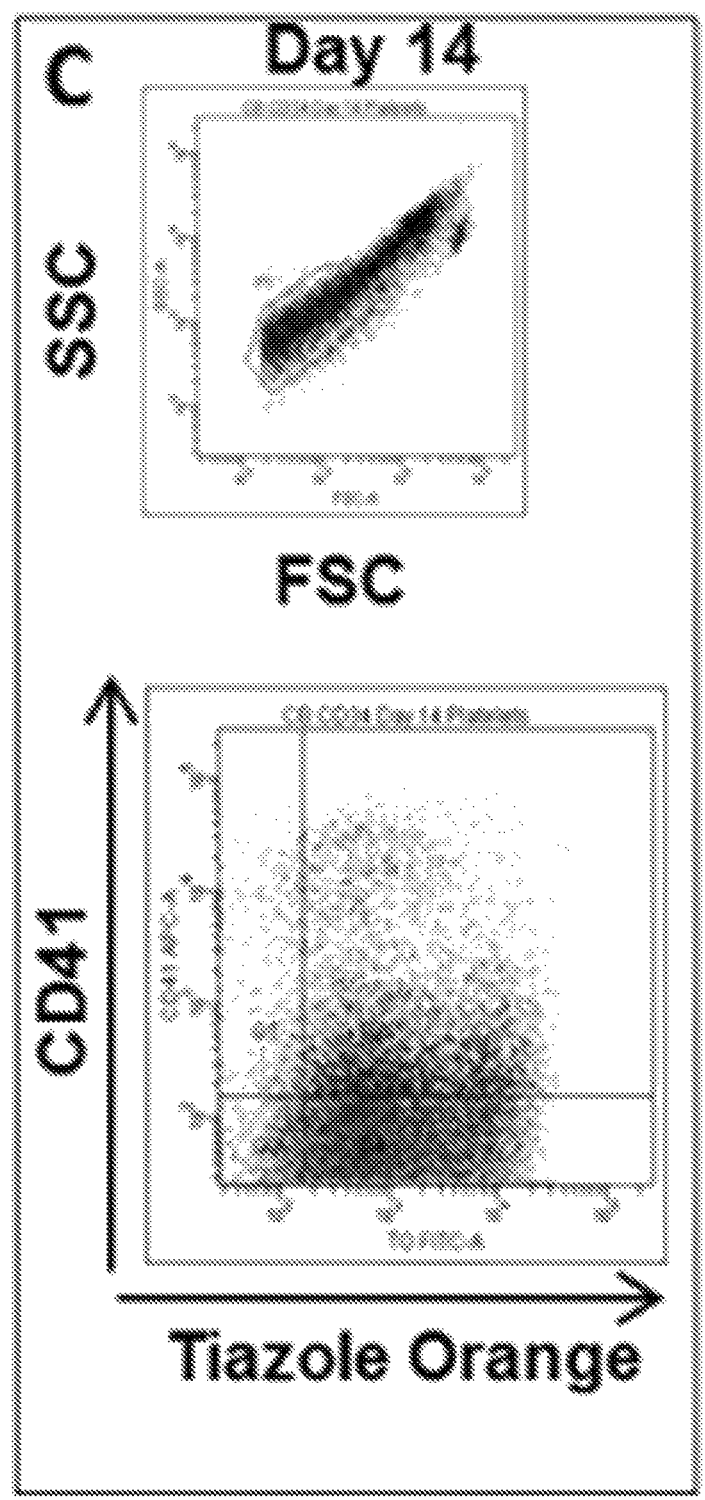

The results indicated that cultures initiated with PB or BM CD34+ cells generate MKs at different stages of development: CD34+/CD41+/CD42b− MK progenitors/precursors (MKPP), immature CD34−/CD41+/CD42b− MK (iMK) and mature CD34−/CD41+/CD42b+ MK (mMK). Notably, CB-derived CD34+ cells can gradually generate a robust MK culture comprising these phenotypically defined MK populations (FIG. 2A and FIG. 2B). MKPP and iMK occur as early as day 4, while mMK are already observed on day 7. By day 12, 77% of the cells were CD41+ cells, of which 23% were MKPP and 74% were mMKs. This corresponds to an absolute yield of 3 MKs from 1 initially plated CD34+ cell. Further, in culture these MKs shed PTLs that were phenotypically comparable to freshly isolated PB PTLs (FIG. 2C). These results indicated that CB CD34+ cells are a reliable source of platelet-producing megakaryocytes.

3. Valproic Acid (VPA) Enhances CD34+ Cells' Ability to Commit and Differentiate into Megakaryocytes (MKs)

Figure 3:
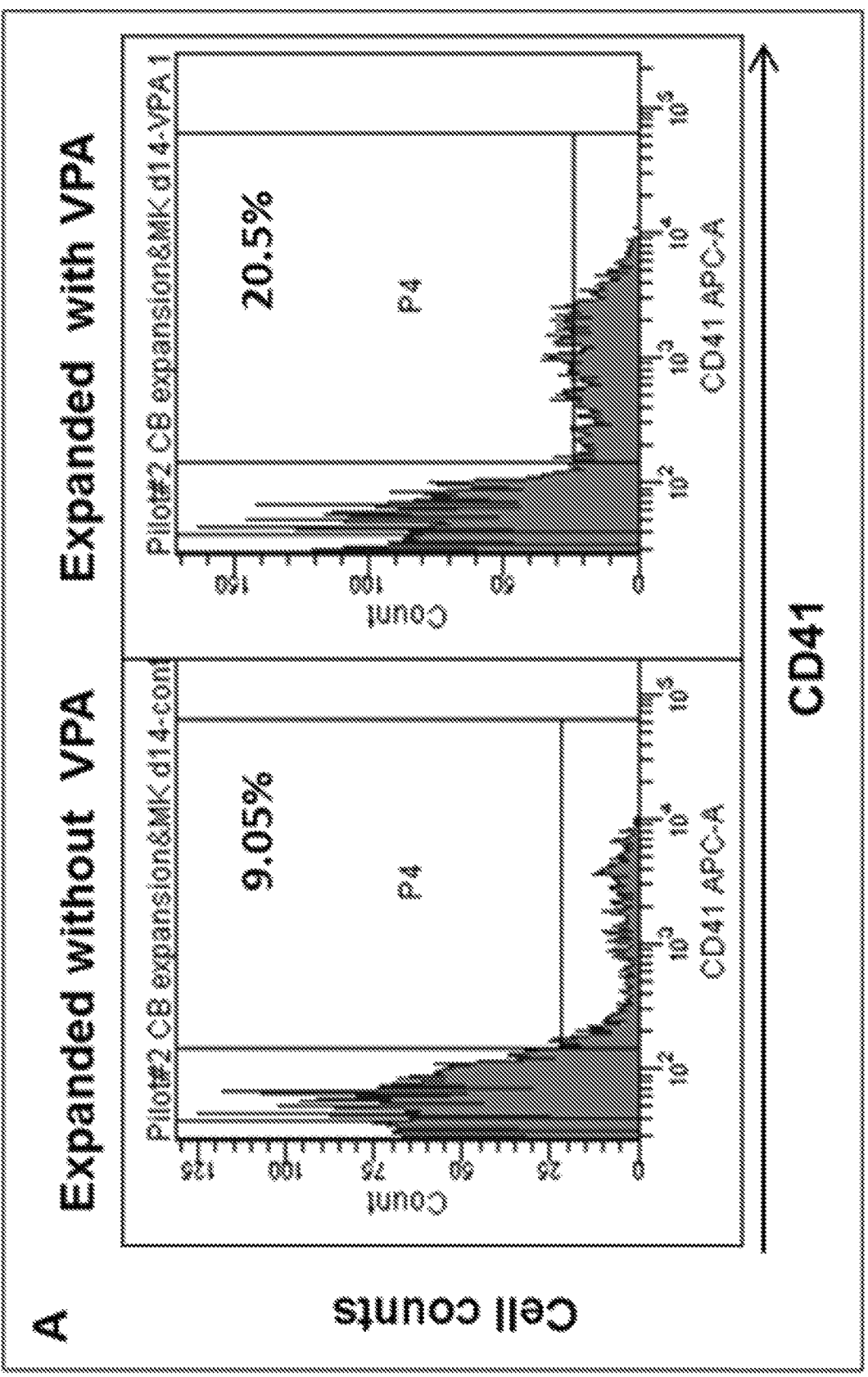
Figure 3:
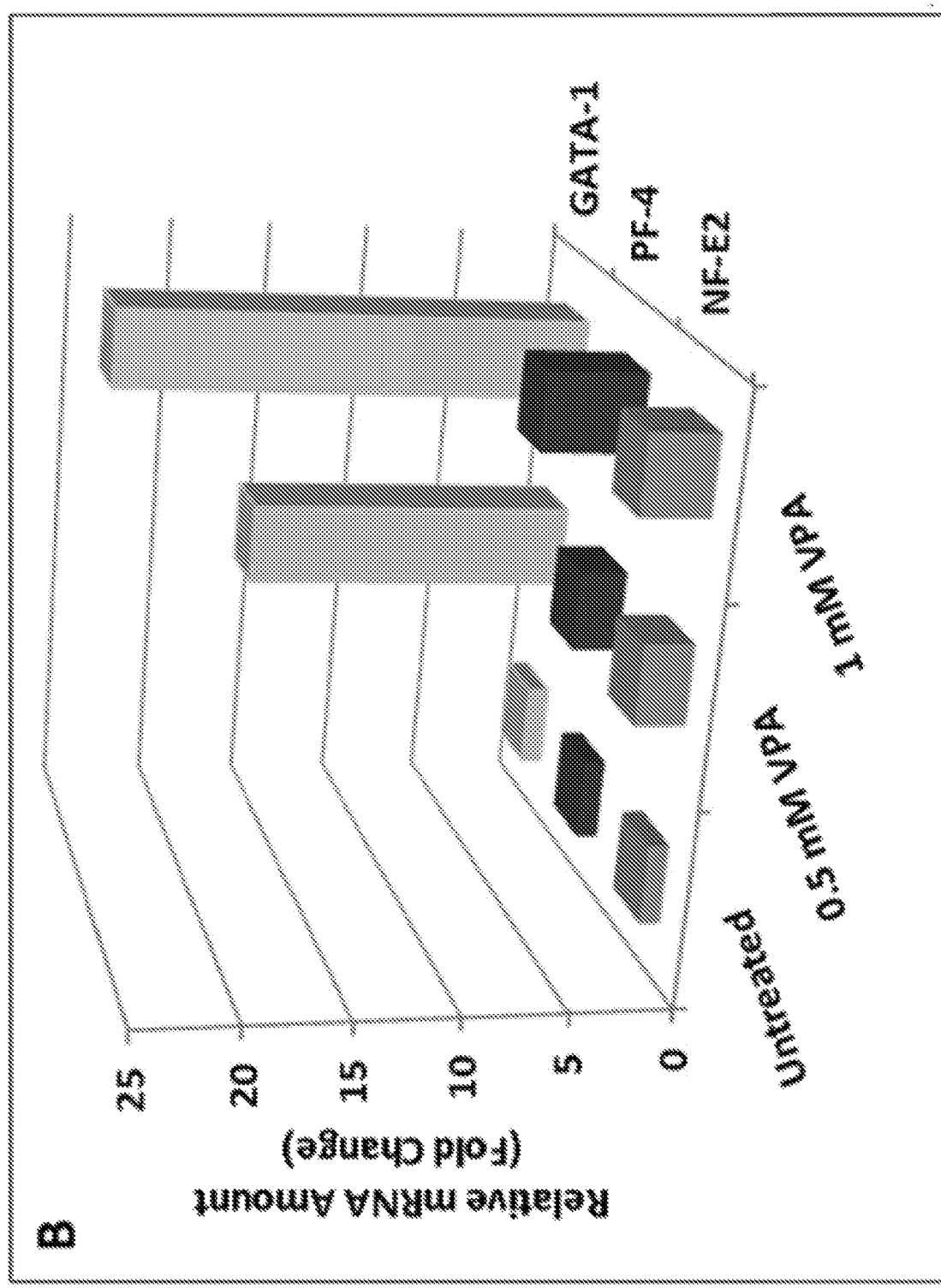

To ensure that exposure to valproic acid (VPA) does not impact the ability of cord blood (CB) CD34+ cells to commit and differentiate into megakaryocytes (MK), the effects of VPA on thrombopoietin (TPO)-mediated MK differentiation and maturation was tested. For this, 50,000 cryopreserved CB CD34+ cells were plated in serum-free (SF) media supplemented with stem cell factor (SCF), interleukin-3 (IL-3), Fms-like tyrosine kinase 3 (FLT-3), and TPO and allowed to expand with or without VPA (testing vs. control), as described in Example 1 above. After 7 days, instead of collecting, the cells were washed to remove VPA and cytokines, and re-plated in SF medium supplemented only with TPO. Approximately 50% more CD41+ MKs were detected in the VPA-expanded cultures than in cultures expanded with only cytokines (FIG. 3A). This corresponded to a final yield of ~40 MKs generated from 1 CD34+ cell plated in the presence of VPA compared to ~5 CD41+ MKs generated by 1 CD34+ cell plated in the absence of VPA. q-PCR analyses confirmed upregulation of MK-specific genes (GATA1, PF4, and NFE2) in the cultures exposed to VPA before MK differentiation (FIG. 3B). These results demonstrate that VPA exposure before MK differentiation improves the final yield of MKs.

4. Ex Vivo Generation of Megakaryocytes (MKs) from Valproic Acid (VPA)-Expanded Cord Blood (CB) CD34+ Cells Cord blood (CB) CD34+ cells were obtained and subjected to the following treatment (CC #15):

Day 0:

The CB CD34+ cells were primed with a cytokine cocktail and plated in serum-free (SF) culture (Stemline media). The cytokine cocktail included stem cell factor (SCF) at an amount of 150 ng/mL, interleukin-3 (IL-3) at an amount of 50 ng/mL, Fms-like tyrosine kinase 3 (FLT-3) at an amount of 100 ng/mL, and thrombopoietin (TPO) at an amount of 100 ng/mL.

Day 1:

1 mM valproic acid (VPA) was added to the SF culture.

Days 1 Through 5:

The cells were allowed to expand in the SF culture.

Days 5 Through 12:

The cells were re-plated in Stemline media with 150 ng/mL SCF and 100 ng/mL TPO and collected at day 12.

Figure 4:
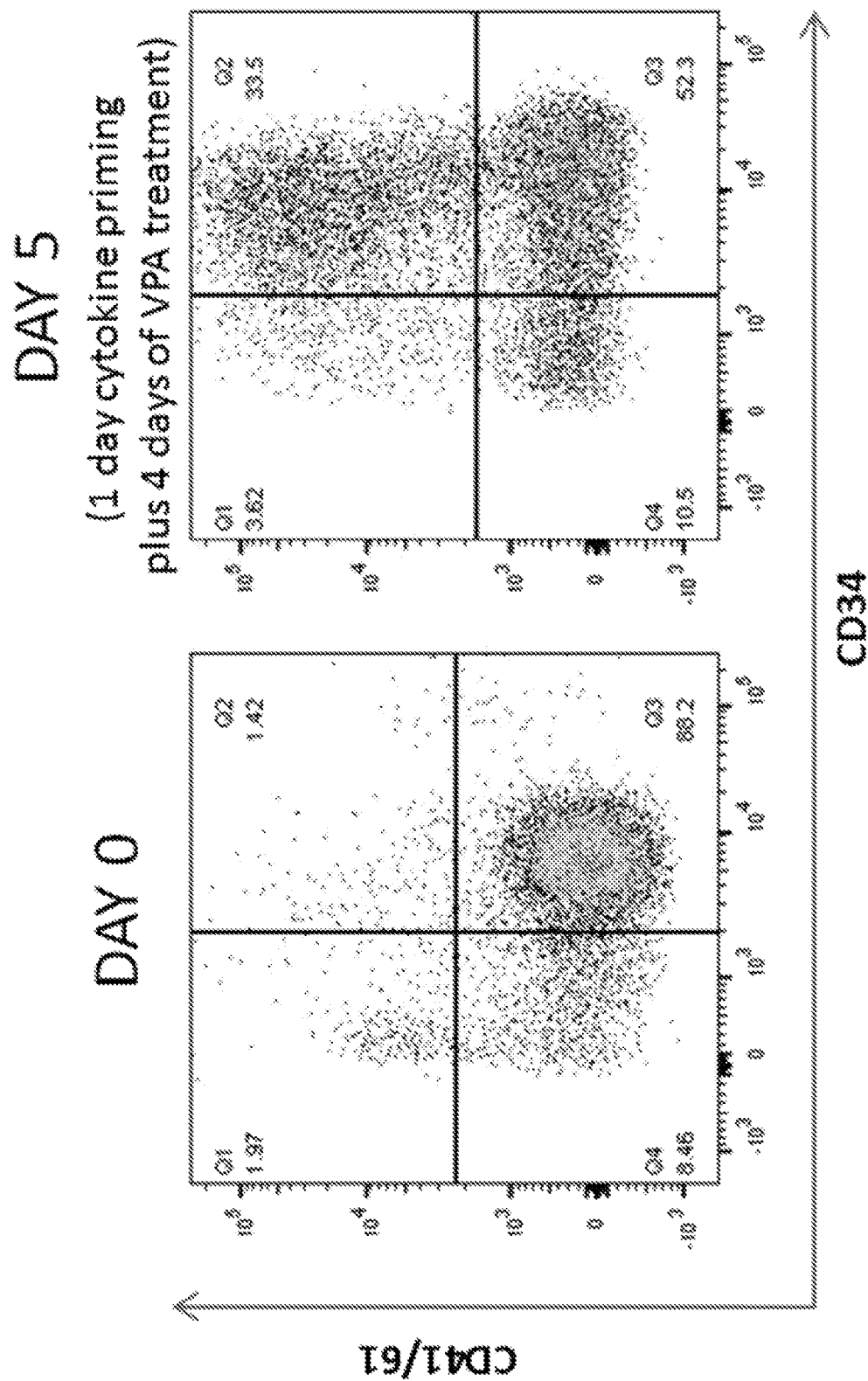
Figure 4:
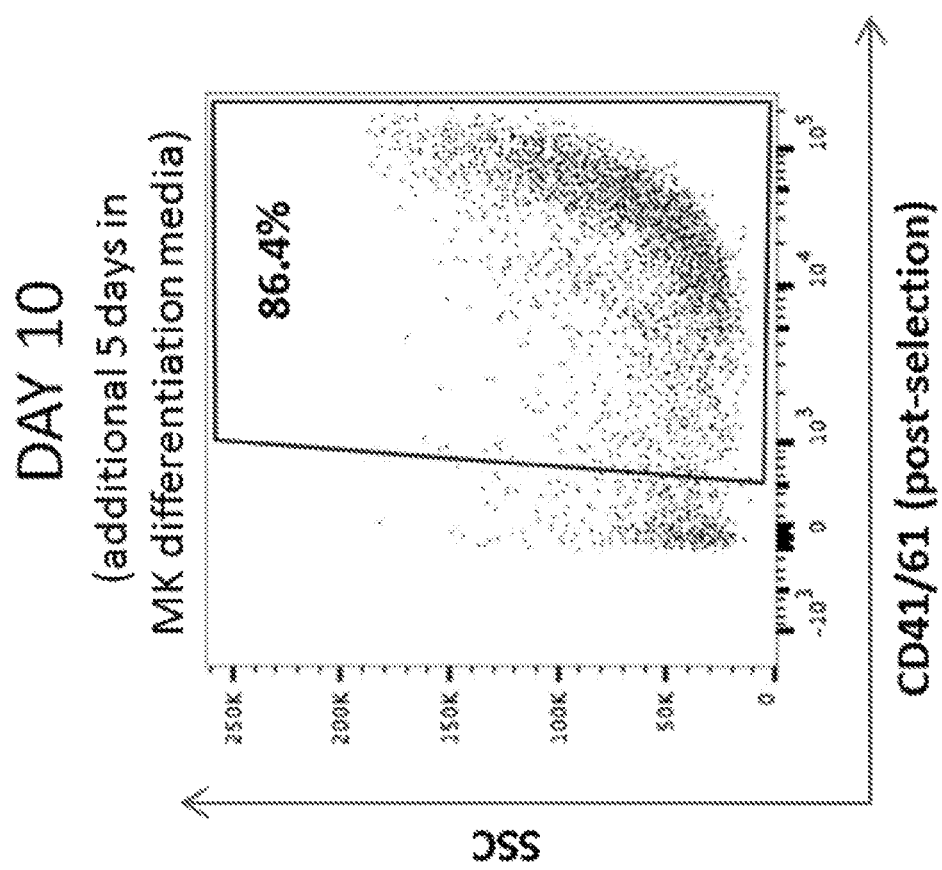

The results, shown in FIG. 4, indicated that at day 0, there was a strong bias to CD34+ cells. By day 5, some differentiation had begun to set in, but there was still notable amount of CD34+ cells. After an additional 5 days in the differentiation media, at day 10, 86.4% of the megakaryocytes (MKs) had differentiated into CD41+/CD61+ MKs.

5. Megakaryocyte (MK) Cultures Generated from Valproic Acid (VPA)-Expanded Cord Blood (CB) CD34+ Cells are Capable of Forming Colony-Forming Units (CFU).

Cord blood (CB) CD34+ cells were obtained and subjected to the following treatments.

Treatment 1: (CC #11)

Days 0 Through 5:

The CB CD34+ cells were primed with a cytokine cocktail and plated in serum-free (SF) culture (Stemline media). The cytokine cocktail included stem cell factor (SCF) at an amount of 150 ng/mL, interleukin-3 (IL-3) at an amount of 50 ng/mL, Fms-like tyrosine kinase 3 (FLT-3) at an amount of 100 ng/mL, and thrombopoietin (TPO) at an amount of 100 ng/mL. The cells were allowed to expand in the culture.

Days 5 Through 8:

The cells were re-plated in Stemline media with 150 ng/mL SCF and 100 ng/mL TPO. The cells were allowed to expand in the culture.

Days 8 Through 12:

The cells were re-plated in Stemline media with 100 ng/mL TPO only.

Treatment 2: (CC #14)

Days 0 Through 5:

The CB CD34+ cells were primed with a cytokine cocktail and plated in serum-free (SF) culture (Stemline media). The cytokine cocktail included stem cell factor (SCF) at an amount of 150 ng/mL, interleukin-3 (IL-3) at an amount of 50 ng/mL, Fms-like tyrosine kinase 3 (FLT-3) at an amount of 100 ng/mL, and thrombopoietin (TPO) at an amount of 100 ng/mL. The cells were allowed to expand in the culture.

Days 5 Through 8:

The cells were re-plated in Stemline media with 10 ng/mL SCF and 100 ng/mL TPO. The cells were allowed to expand in the culture.

Days 8 Through 12:

The cells were re-plated in Stemline media with 100 ng/mL TPO only.

Treatment 3: (CC #17)

Day 0:

The CB CD34+ cells were primed with a cytokine cocktail and plated in serum-free (SF) culture (Stemline media).

The cytokine cocktail included stem cell factor (SCF) at an amount of 150 ng/mL, interleukin-3 (IL-3) at an amount of 50 ng/mL, Fms-like tyrosine kinase 3 (FLT-3) at an amount of 100 ng/mL, and thrombopoietin (TPO) at an amount of 100 ng/mL.

Day 1:

1 mM valproic acid (VPA) was added to the SF culture.

Days 1 Through 5:

The cells were allowed to expand in the SF culture.

Days 5 Through 8:

The cells were re-plated in Stemline media with 150 ng/mL SCF and 100 ng/mL TPO.

Days 8 Through 12:

The cells were re-plated in Stemline media with only 100 ng/mL TPO.

Treatment 4: (CC #19)

Day 0:

The CB CD34+ cells were primed with a cytokine cocktail and plated in serum-free (SF) culture (Stemline media). The cytokine cocktail included stem cell factor (SCF) at an amount of 150 ng/mL, interleukin-3 (IL-3) at an amount of 50 ng/mL, Fms-like tyrosine kinase 3 (FLT-3) at an amount of 100 ng/mL, and thrombopoietin (TPO) at an amount of 100 ng/mL.

Day 1:

1 mM valproic acid (VPA) was added to the SF culture.

Days 1 Through 5:

The cells were allowed to expand in the SF culture.

Days 5 Through 8:

The cells were re-plated in Stemline media with 10 ng/mL SCF and 100 ng/mL TPO.

Days 8 Through 12:

The cells were re-plated in ½ volume Stemline media with 10 ng/mL SCF and 100 ng/mL TPO.

Figure 5:
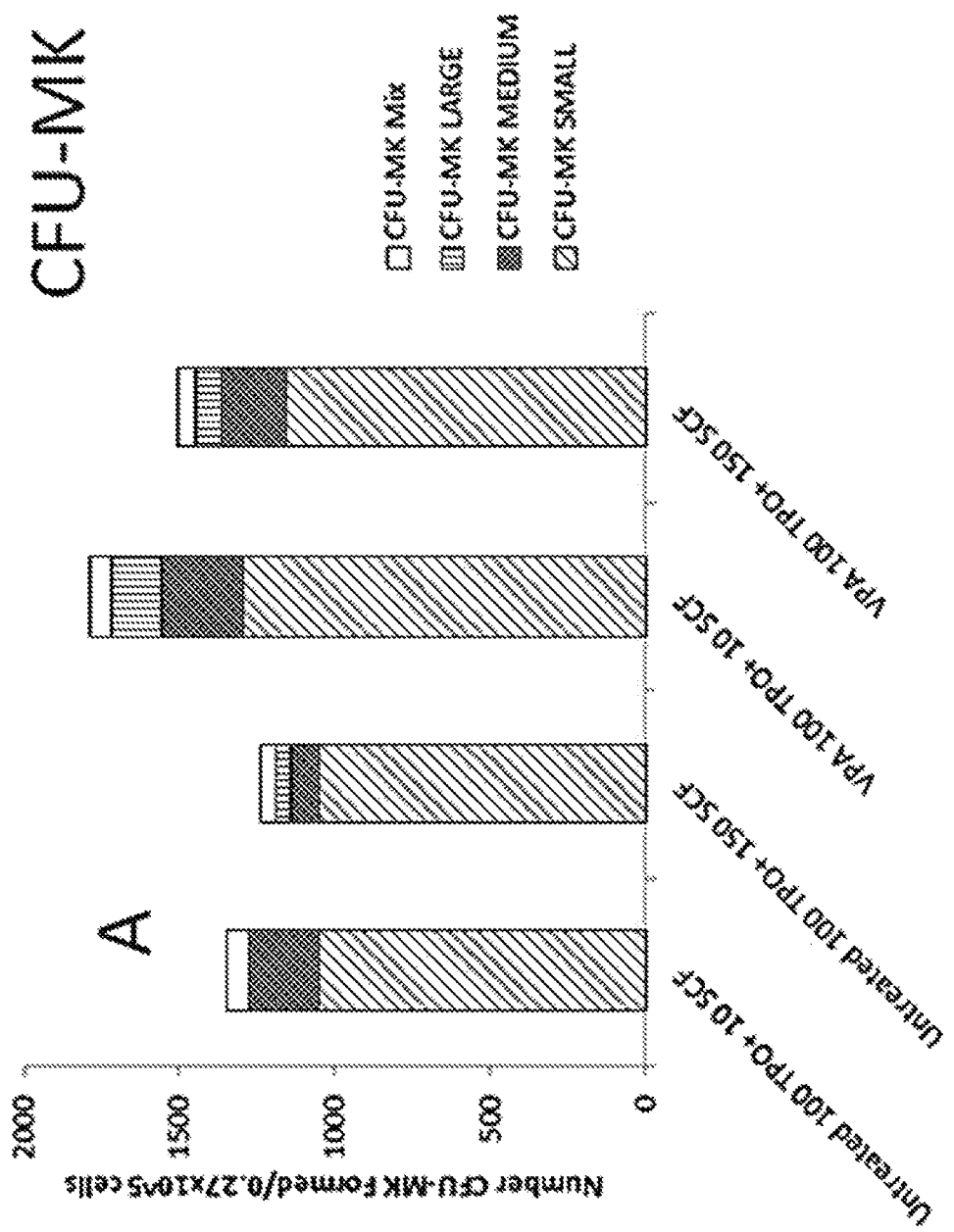
Figure 5:
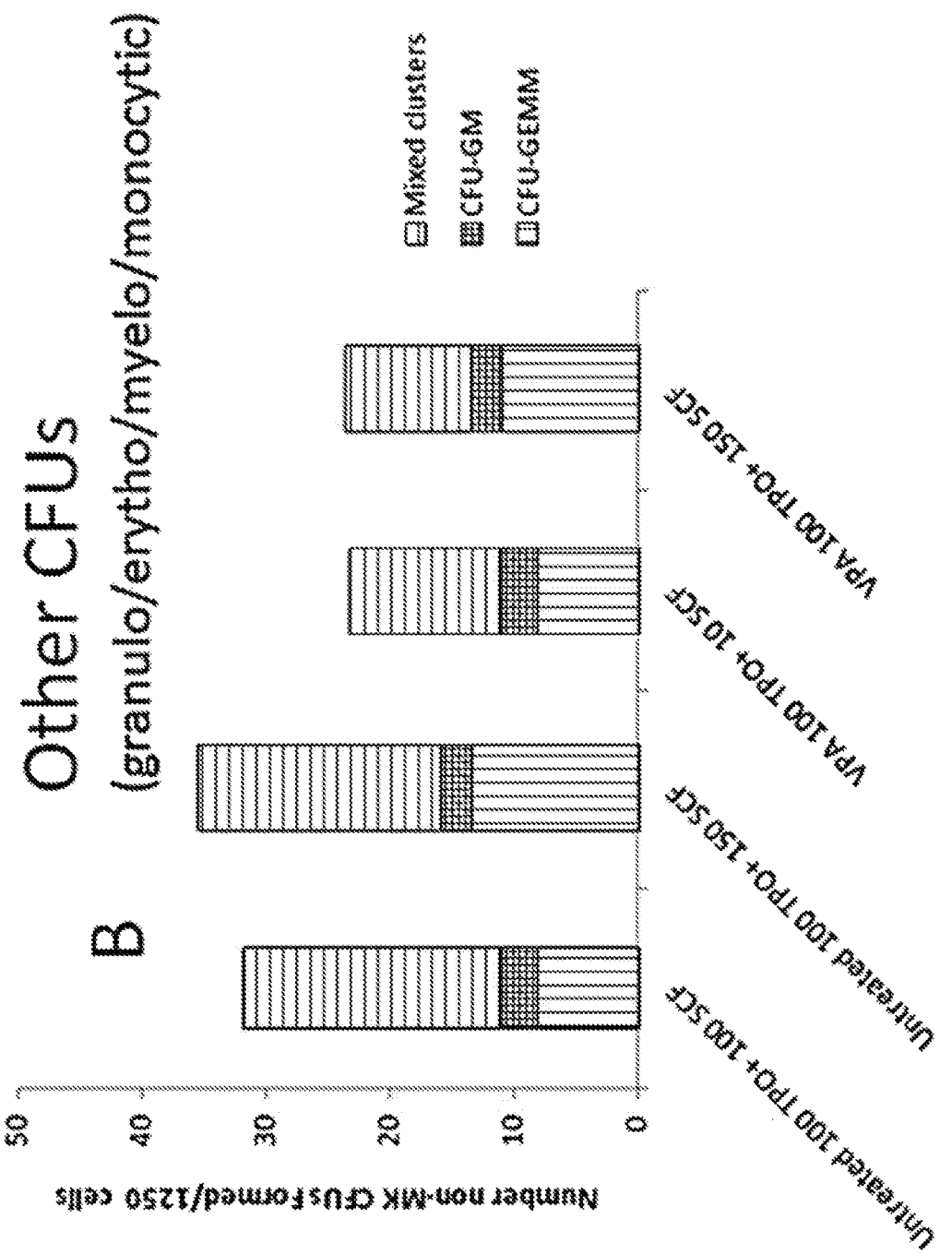

The results, shown in FIG. 5, indicated a robust number of CFU-MKs (FIG. 5A), ranging from large, medium, and small in size, compared to other CFUs (FIG. 5B), which were considerably less in number and were mostly mixed clusters. The first column of each of FIG. 5A and FIG. 5B correspond to Treatment 1 (CC #11), the second column corresponds to Treatment 2 (CC #14), the third column corresponds to Treatment 3 (CC #17), and the fourth column corresponds to Treatment 4 (CC #19).

6. CD61+ Megakaryocytes (MKs) Isolated from Valproic Acid (VPA)-Expanded Cultures are Amenable to Cryopreservation

A.

Cord blood (CB) CD34+ cells were obtained and subjected to various culture protocols (CC #5, CC #15, CC #16, and CC #17 as described herein). CD61+ megakaryocytes (MKs) were immunomagnetically purified from the resultant differentiated megakaryocyte products. The CD61+ MKs were cryopreserved for three (3) months, alongside unpurified, heterogeneous megakaryote (MK) products. The purified CD61+ MKs and heterogeneous MK products were then thawed and evaluated for phenotype. The results for the purified CD61+ MKs are shown in TABLE 1 below, whereas the results for the heterogeneous MK products are shown in TABLE 2 below.

TABLE 1

Viability and MK Phenotype recover prior and post-cryopreservation of CD61+ Purified MK cell product.
Purified MK cryopreserved post-expansion (n = 3 CBUs)

| TNCs (x10⁶) | | | | MK Phenotype | | |
|---|---|---|---|---|---|---|
| | | | | Percent (%) | Percent (%) | Percent (%) |
| Viable Cells Prior to Cryo. | Viable Cells Post-Thaw | Percent (%) Recovery | Percent (%) Viability | CD41+ MK (Prior) | CD41+ MK (Post) | CD41+ MK Recovery |
| 1.07 ± 0.61 | 0.67 ± 0.32 | 67.75 ± 15.9 | 71.70 ± 7.24 | 92.83 ± 4.7 | 92.37 ± 5.52 | 99.47 ± 4.25 |

TABLE 2

Viability and MK Phenotype recover prior and post-cryopreservation of heterogeneous MK cell product.
Heterogeneous MK cultures cryopreserved post-expansion (n = 2 CBUs)

| TNCs (x10⁶) | | | | MK Phenotype | | |
|---|---|---|---|---|---|---|
| | | | | Percent (%) | Percent (%) | Percent (%) |
| Viable Cells Prior to Cryo. | Viable Cells Post-Thaw | Percent (%) Recovery | Percent (%) Viability | CD41+ MK (Prior) | CD41+ MK (Post) | CD41+ MK Recovery |
| 3.5 ± 2.12 | 1.18 ± 0.03 | 41 ± 24.04 | 63.5 ± 9.19 | 29.85 ± 0.35 | 24.7 ± 5.37 | 118.65 ± 27.79 |

B.

Figure 6:
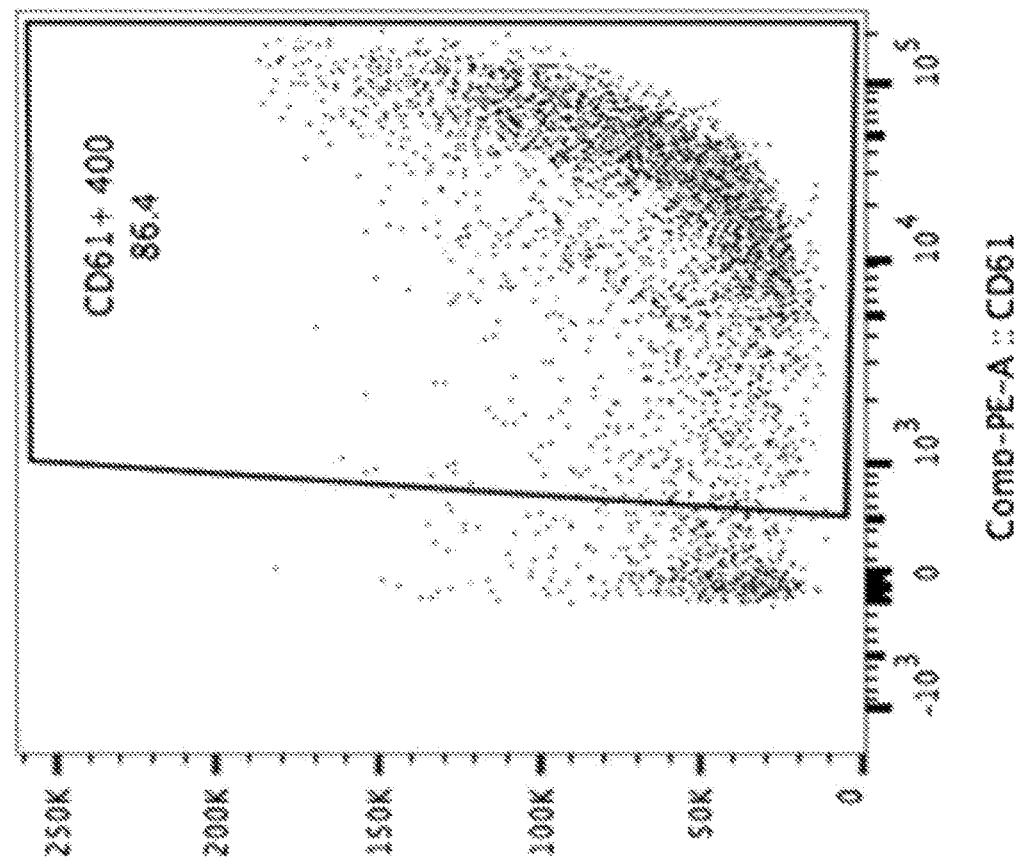
Figure 6:
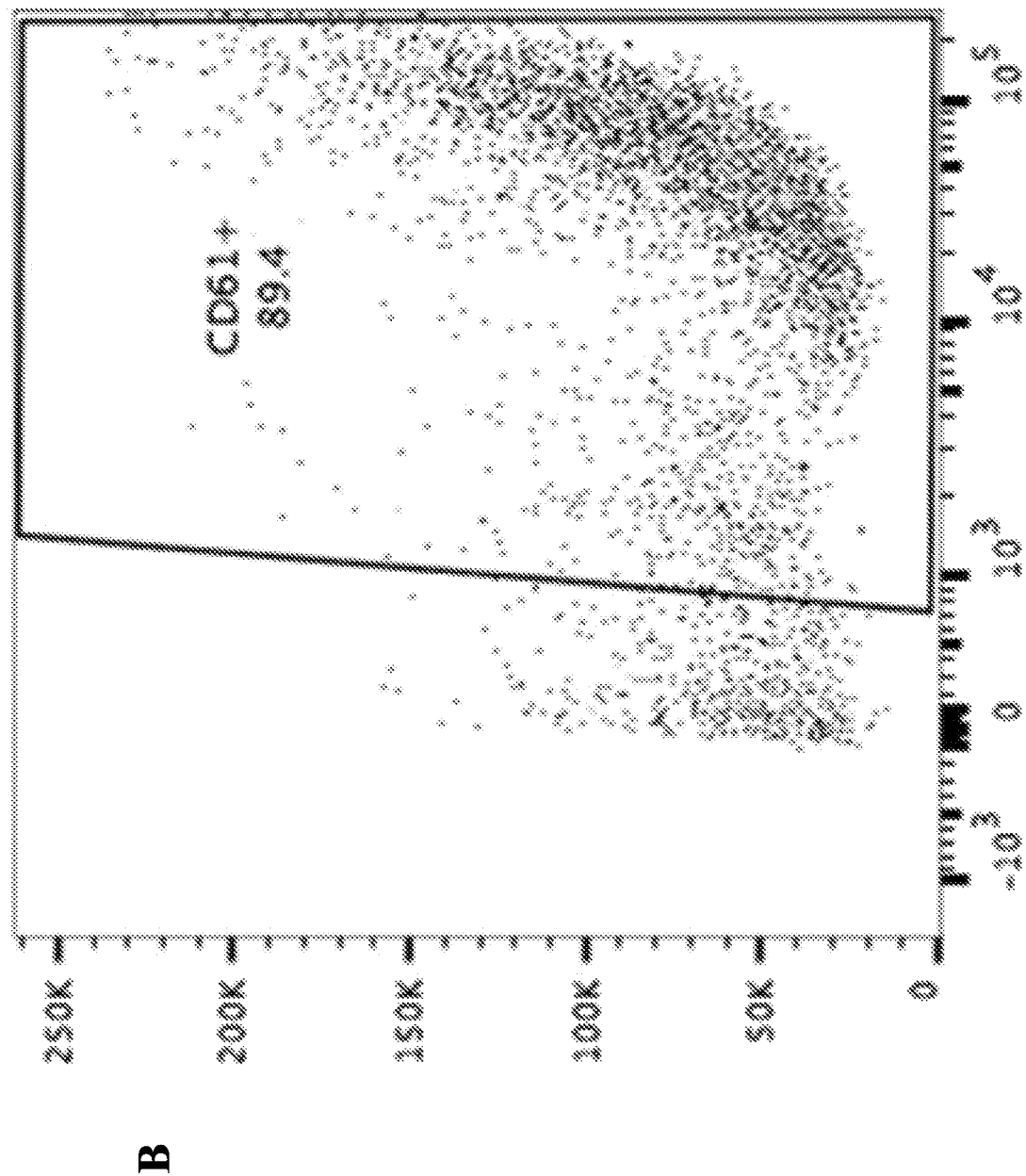

Cord blood (CB) CD34+ cells were obtained and were subjected to culture protocol CC #17 as described in Treatment 3 of Example 4, supra. CD61+ megakaryocytes (MKs) were immunomagnetically purified from the resultant differentiated megakaryocyte products. The CD61+ MKs were cryopreserved for three (3) months. The results indicated that prior to cryopreservation, 70.9% of the MKs were viable, and after thawing, 68.4% were viable, a surprisingly high level of preservation of MKs post-thawing. The population of the MKs after thawing was distributed as follows: CD34+/CD41+ made up 0.9% of the total MK population, CD41+/CD42− made up 27.4% of the total MK population, and CD41+/CD42+ made up 65.5% of the total MK population. As shown in FIG. 6A, prior to cryopreservation, 86.4% of the megakaryocytes (MKs) isolated from VPA-expanded cultures were CD61+ cells, whereas shown in FIG. 6B, post-thawing 89.4% of the megakaryocytes (MKs) isolated from the VPA-expanded cultures were CD61+ cells.

Figure 7A:
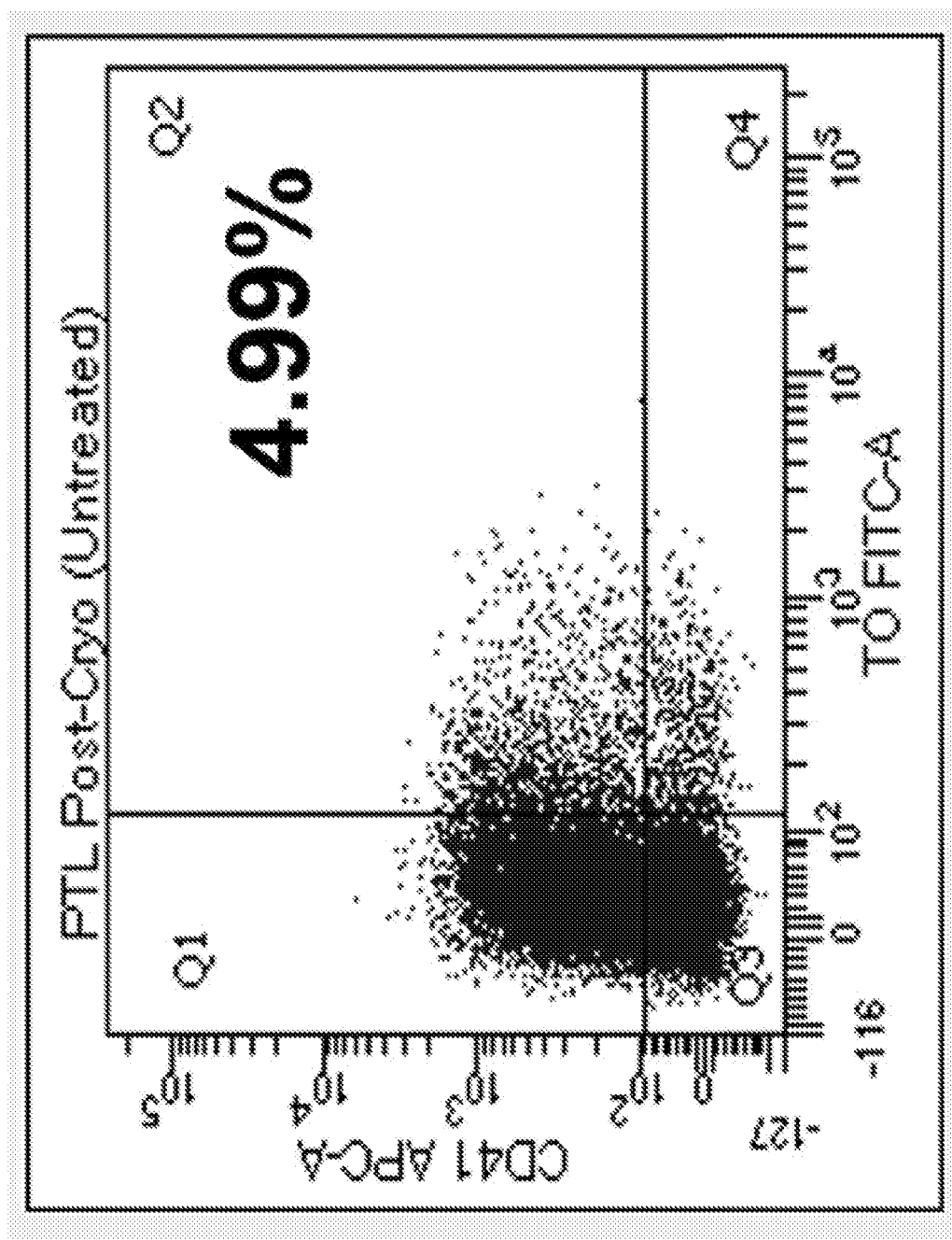
Figure 7A:
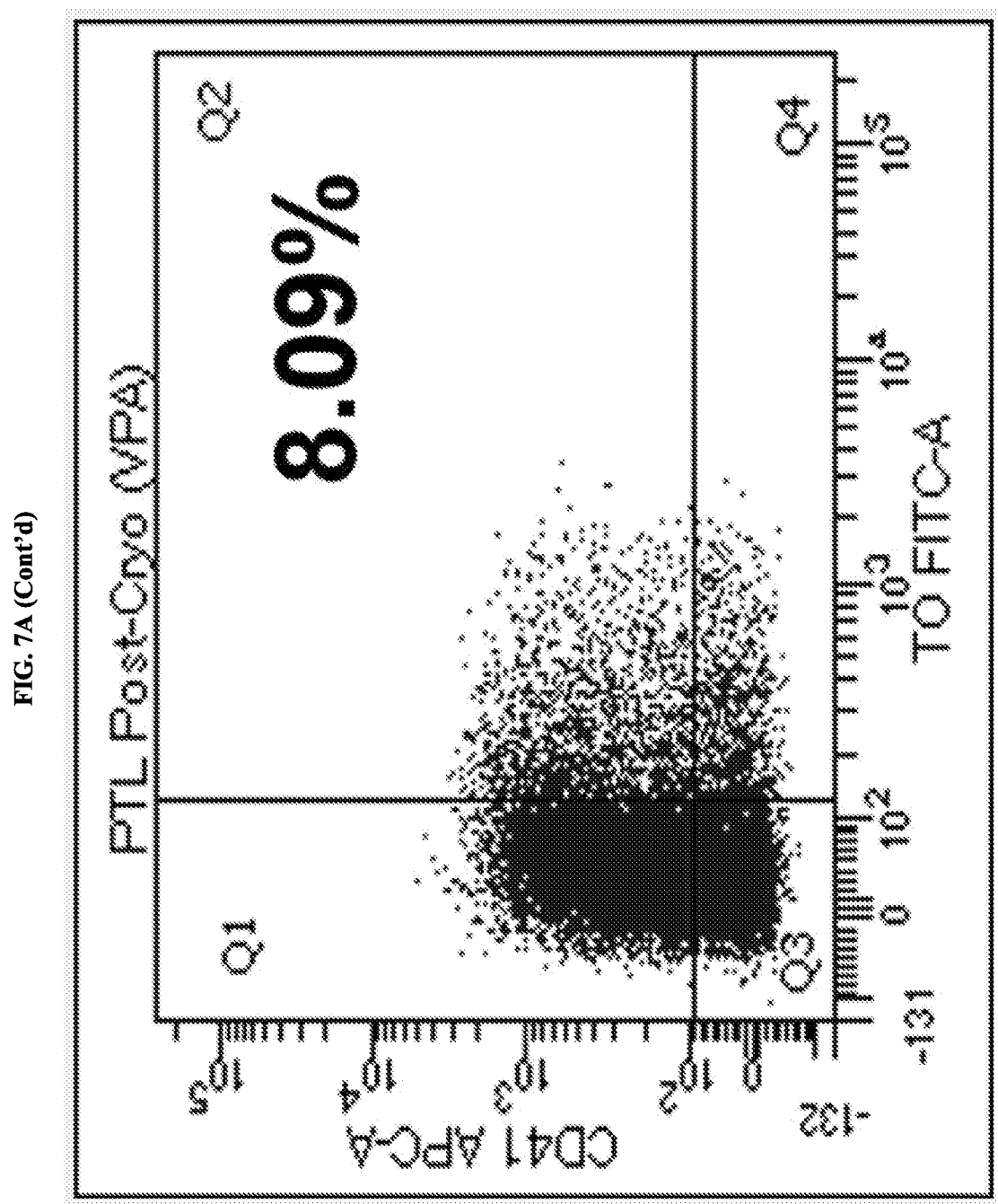
Figure 7B:
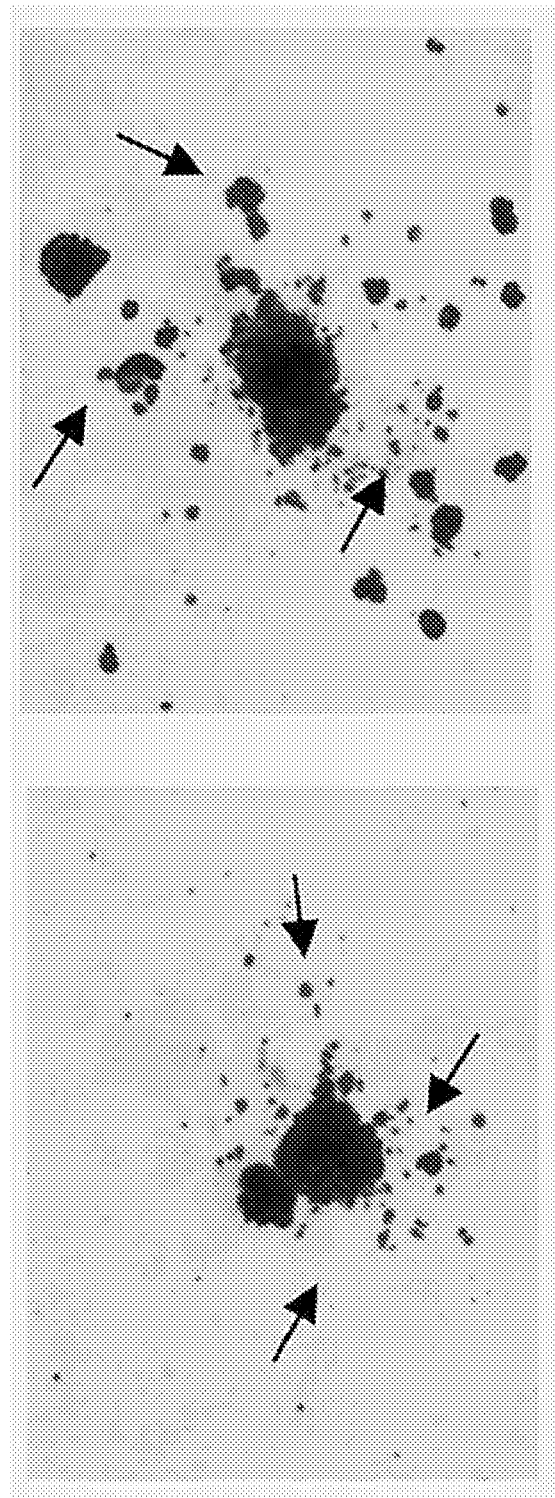

C. Cryopreserved MK generated from HSC expanded in the presence of cytokines alone or cytokines plus VPA (subjected to culture protocol CC #17) were thawed and evaluated for their ability to release platelets ex vivo and to form CFU-MK. The results are shown in FIG. 7A and FIG. 7B (thiazole orange staining).

7. Integrated Culture Protocol

Cord blood (CB) CD34+ cells are obtained and are subjected to the following treatment.

Day 0:

The CB CD34+ cells are primed with a cytokine cocktail and plated in serum-free (SF) culture with stem cell factor (SCF) at an amount of 150 ng/mL, IL-3 at an amount of 50 ng/mL, Fms-like tyrosine kinase 3 (FLT-3) at an amount of 100 ng/mL, and thrombopoietin (TPO) at an amount of 100 ng/mL.

Day 1:

1 mM valproic acid (VPA) and 50 ng/mL IL-6 is added to the SF culture.

Days 1 Through 7:

The cells are allowed to expand in the SF culture.

Day 7:

The cells are re-plated in SF media with SCF at an amount ranging from 10 ng/mL to 150 ng/mL and TPO at an amount of 100 ng/mL.

Days 7 Through 10:

The cells are allowed to expand and differentiate.

Day 10:

The cells are re-plated in SF media with TPO at an amount of 100 ng/mL.

Days 10 Through 14:

The cells are allowed to differentiate.

Day 14:

The cells are collected, quantified and characterized.

8. Human MK and Platelets Engraftment in Immunocompromised NSG Mice

Figure 8A:
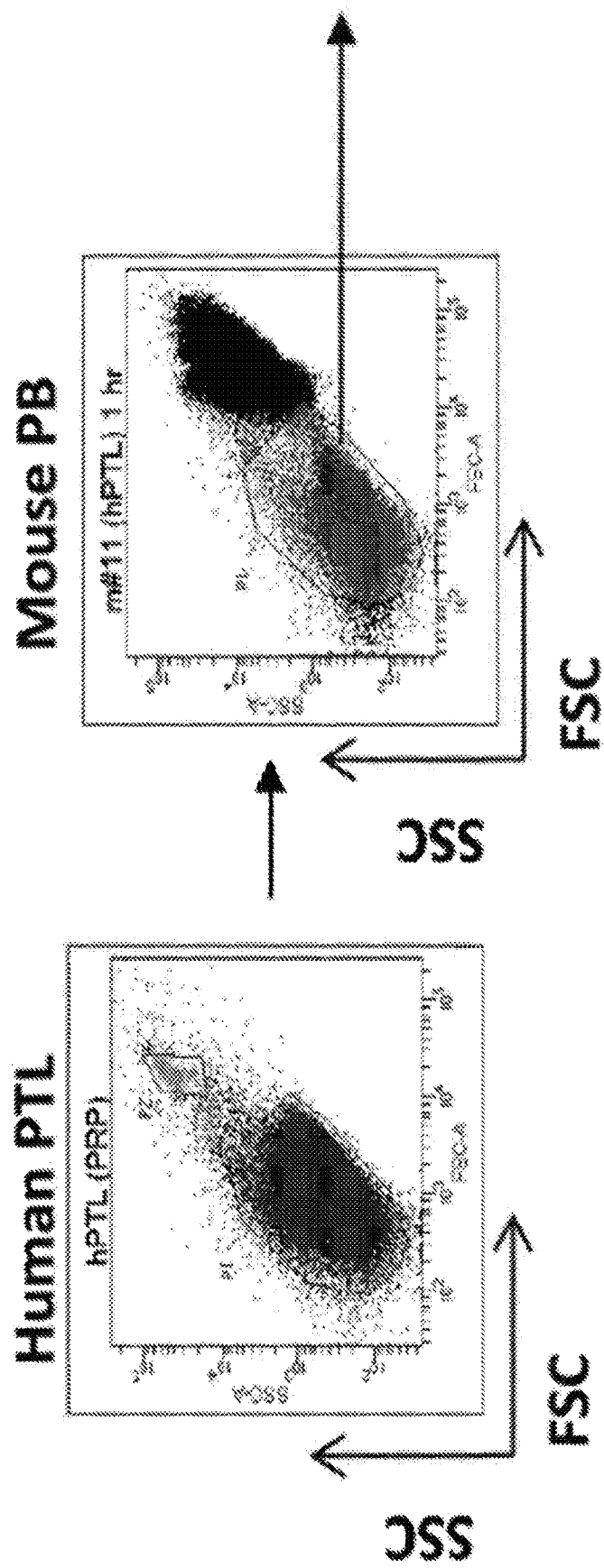
Figure 8B:
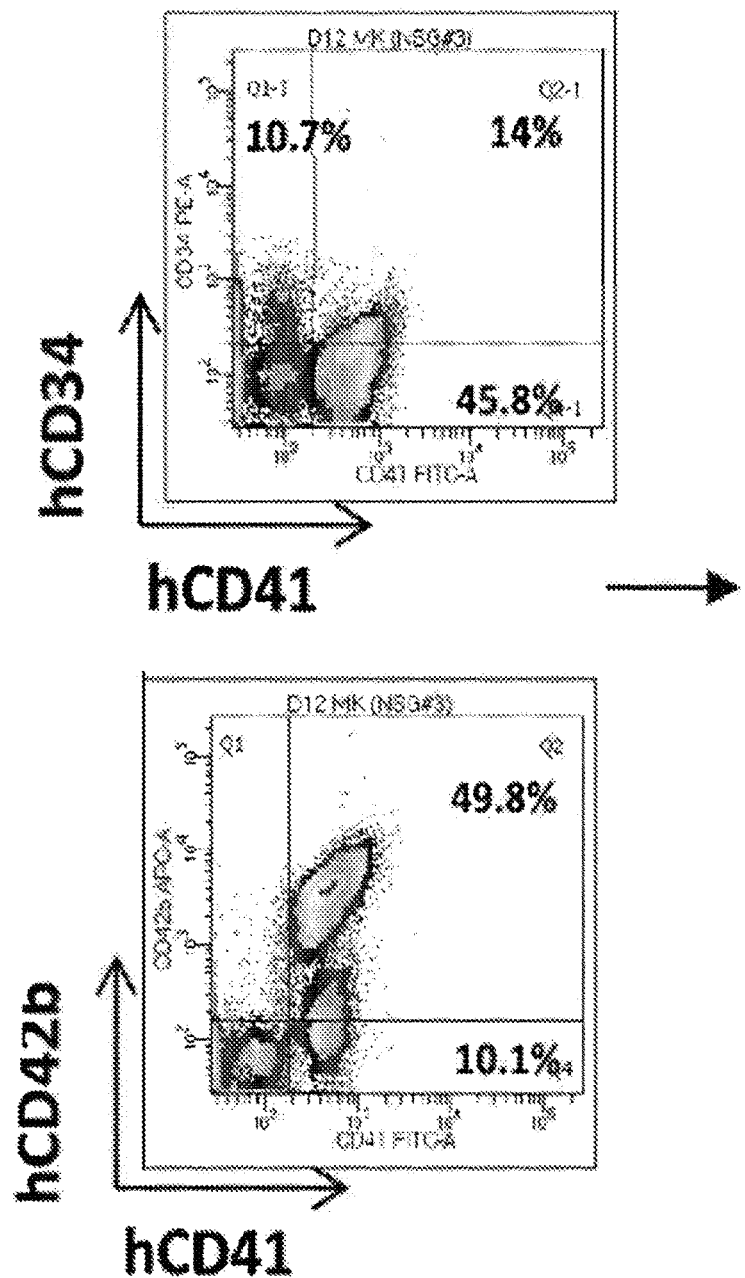
Figure 8C:
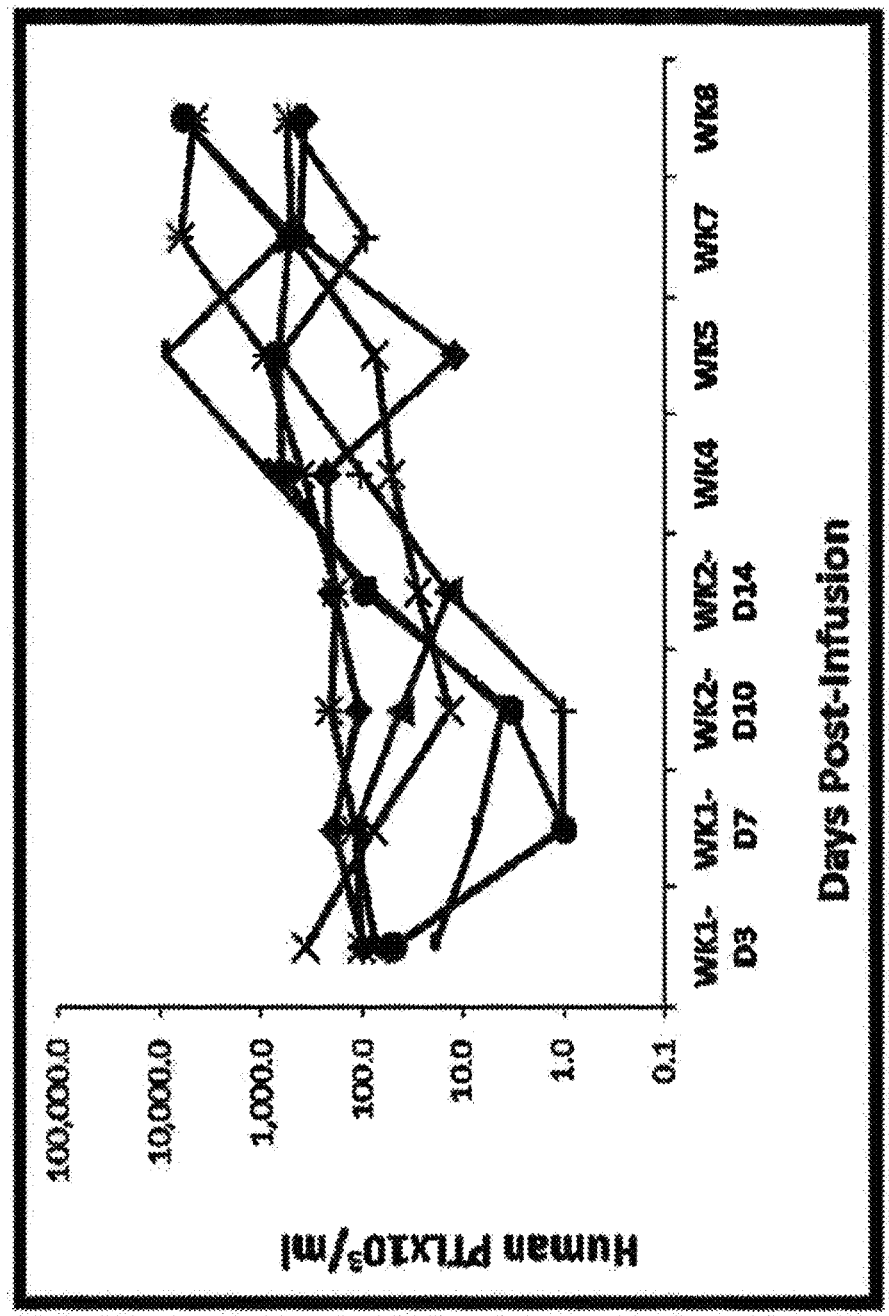
Figure 8D:
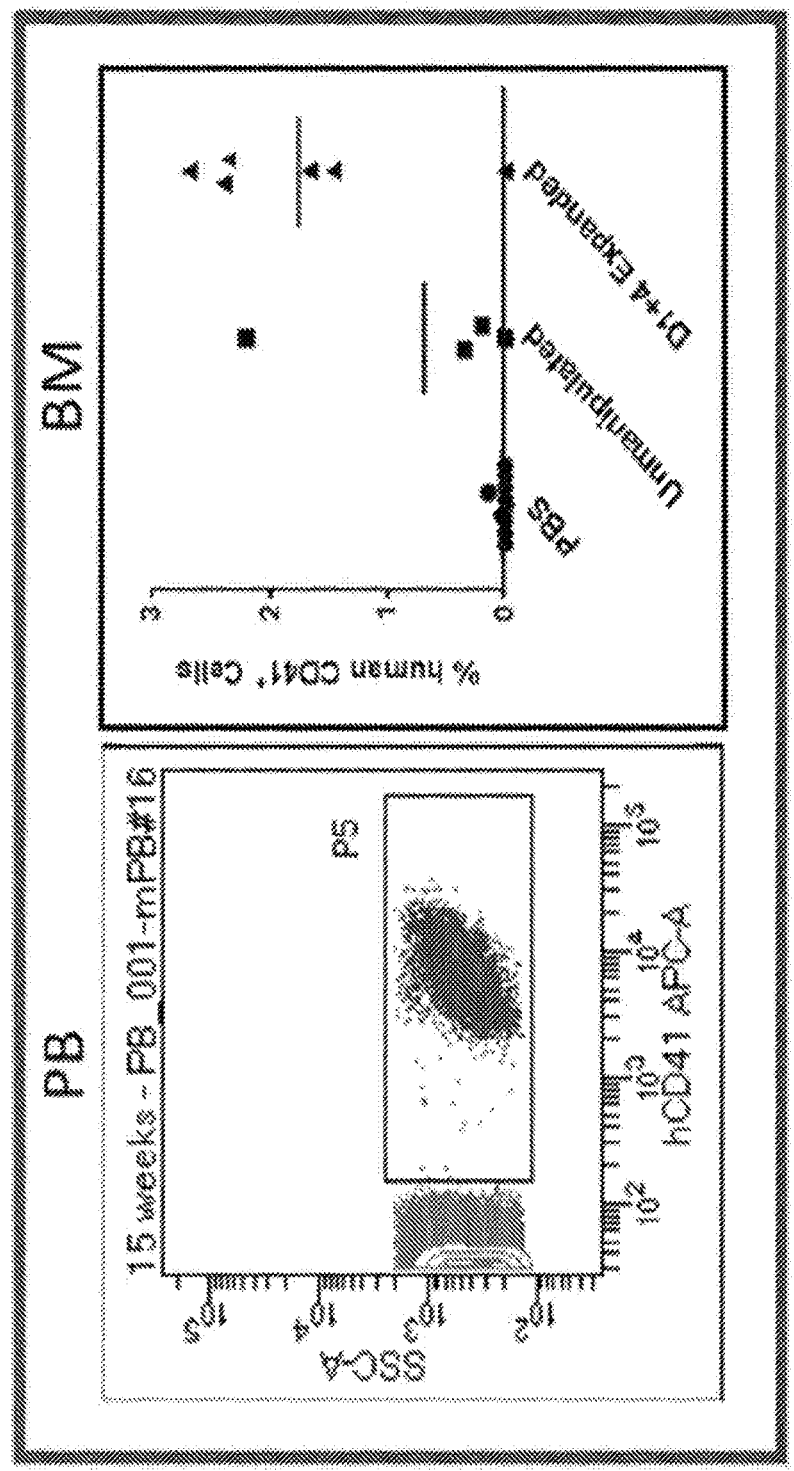
Figure 8E:
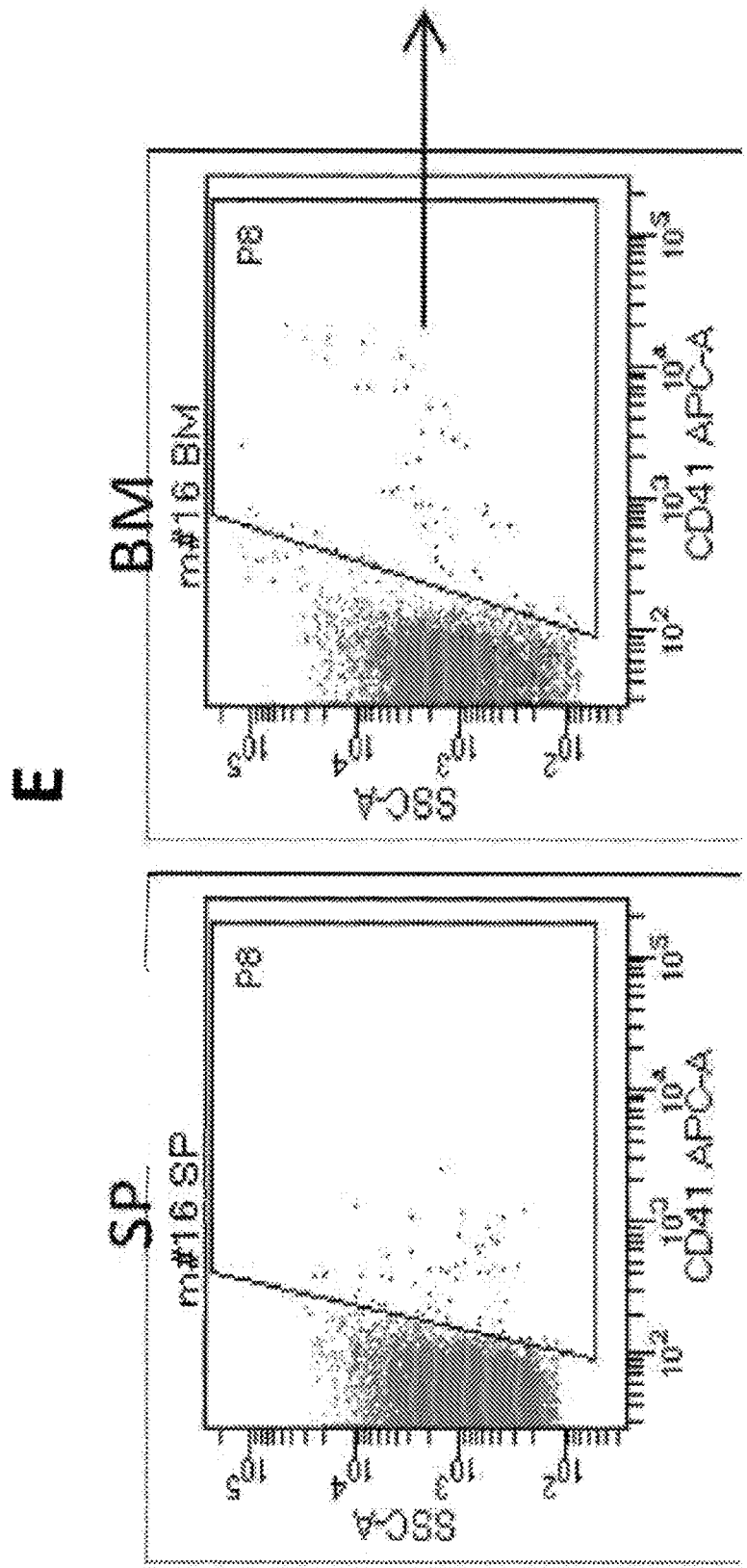

The ability of ex vivo generated MK to generate platelets in vivo after infusion in immunocompromised NSG mice was examined. First, fresh human platelet-rich plasma was infused in recipient animals and the presence of human PTL was assessed in the mouse peripheral blood (mPB) between about 1 hour and 5 days post-infusion (FIG. 8A). The size and light scatter properties of the human PTL coupled with human CD41 labeling were used as positive controls for detection of human PTL detection in mPB after infusion with MK cultures. MK cultures were generated ex vivo and harvested, quantified, and evaluated phenotypically and infused into four different experimental groups: a first group, which received MK populations generated in basic MK culture system (Day 0-7 100 ng/ml SCF and 50 ng/ml TPO in SF QBSF media followed by day 8-10 in SF QBSF media with 50 ng/ml TPO only) (Iancu-Rubin et al. Blood 2011, Exp Hematol 2012 and 2014, Leukemia 2017); a second group, which received MK generated in the presence of cytokines alone (CC #10); a third group, which received MK generated in the presence of cytokines plus VPA (CC #16); and a fourth group, which received fresh purified CD61+ MK. MK cultures (CC #16) infused in these three groups comprised a heterogeneous MK population and the total number of cells infused varied between about 0.6 to about 5 million (see TABLE 3 below). As illustrated in FIG. 8, infusion of ex vivo generated MK product lead to detectable hPTL into the mPB of NSG recipient mice and CD41+ cells into the mouse bone marrow (mBM).

The results surprisingly indicated that the degree of in vivo hPTL production after infusion of a comparable number of MK is greater when MK were generated in basic culture conditions (two-step culture in serum-free media with SCF and TPO only) as compared to MK generated in cultures in the presence of VPA. Without wishing to be bound by theory, the lack of in vivo PTL production after infusion of purified MK was attributed to the limited numbers of MK injected. The conclusion was that ex vivo produced MK cell product derived from CB HSCs comprises not only mMK and iMK capable of immediate PTL release, but also comprises MKP and HPCs which are capable of sustained MK and PTL production.

Figure 8F:
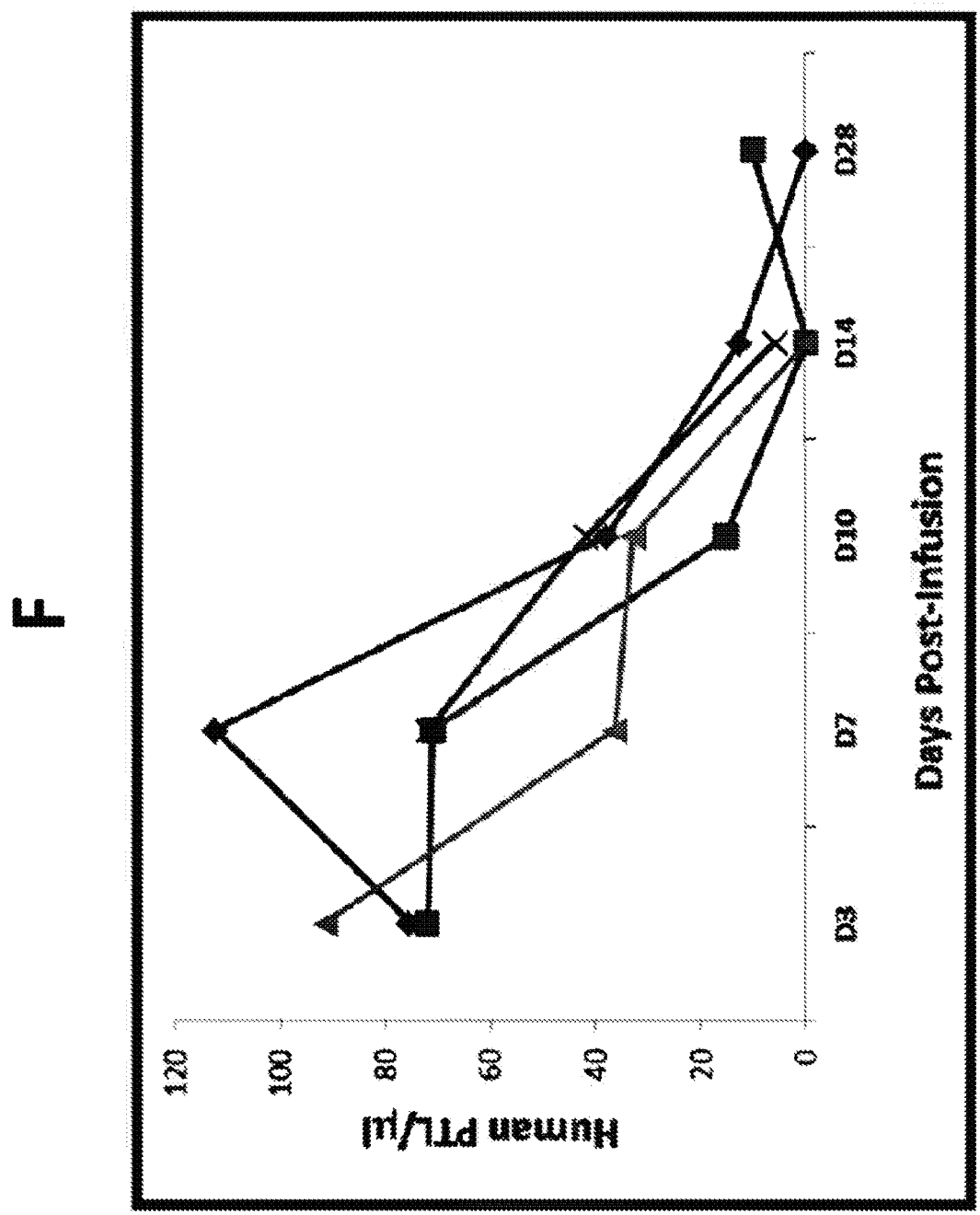

As illustrated in Example 6, expanded MKs are amenable to cryopreservation. Importantly however, they were also capable of in vivo platelet production. More specifically, when either heterogeneous or purified cryopreserved MK were infused in immunocompromised NSG mice, they were capable of in vivo platelet production. Two out of five animals in each group infused with either heterogeneous MK or purified MK cultures released hPTL in vivo. Surprisingly, after the infusion of as few as 0.1 million purified MK, hPTL was observed in the mPB as early as days 3, 7 and 10. However, their numbers declined to undetectable levels at later time points (FIG. 8F). By contrast, in NSG mice infused with heterogeneous MK population, hPTL production was sustained for up to three months, a significantly longer time period than those given purified MK culture. While not wishing to be bound by theory, these findings indicate that purified populations of mature MK may lead to a rapid, early PTL production, a heterogeneous MK population comprised of MK precursors and mature MK may allow for both rapid and sustained PTL production in vivo.

TABLE 3

Assessment of hPTL generated in vivo in NSG mice following infusion of ex vivo generated MK.

| Experimental Group | # TNC/Mouse | # CD41+ Cells Injected | # Mice Injected | # Mice w/ hPTL in PB | # Mice with CD41+ cells in BM |
|---|---|---|---|---|---|
| Basic MK culture (SCF + TPO day 1-7 followed by TPO only d 7-12) | $1\text{-}2.5 \times 10^6$ | $0.5\text{-}1 \times 10^6$ | 8 | 7 | 7 |
| MK culture (cytokines only) (CC#10 Culture stopped at day 10) | $2 \times 10^6$ | $0.08 \times 10^6$ | 10 | 0 | 0 |
| MK culture (cytokines + VPA) (CC#16 culture stopped at day 10) | $0.6\text{-}5 \times 10^6$ | $0.3\text{-}0.5\text{-}1 \times 10^6$ | 20 | 4 | 4 |

TABLE 3-continued

Assessment of hPTL generated in vivo in NSG mice following infusion of ex vivo generated MK.

| Experimental Group | # TNC/Mouse | # CD41+ Cells Injected | # Mice Injected | # Mice w/ hPTL in PB | # Mice with CD41+ cells in BM |
|---|---|---|---|---|---|
| Purified CD61+ MK (cytokines + VPA) (CC#16 culture stopped at day 10 followed by immunomagnetic selection of CD61+ cells) | $0.15 \times 10^6$ | $0.03 \times 10^6$ | 5 | 0 | 0 |

TNC = total nucleated cells.

Figure 9:
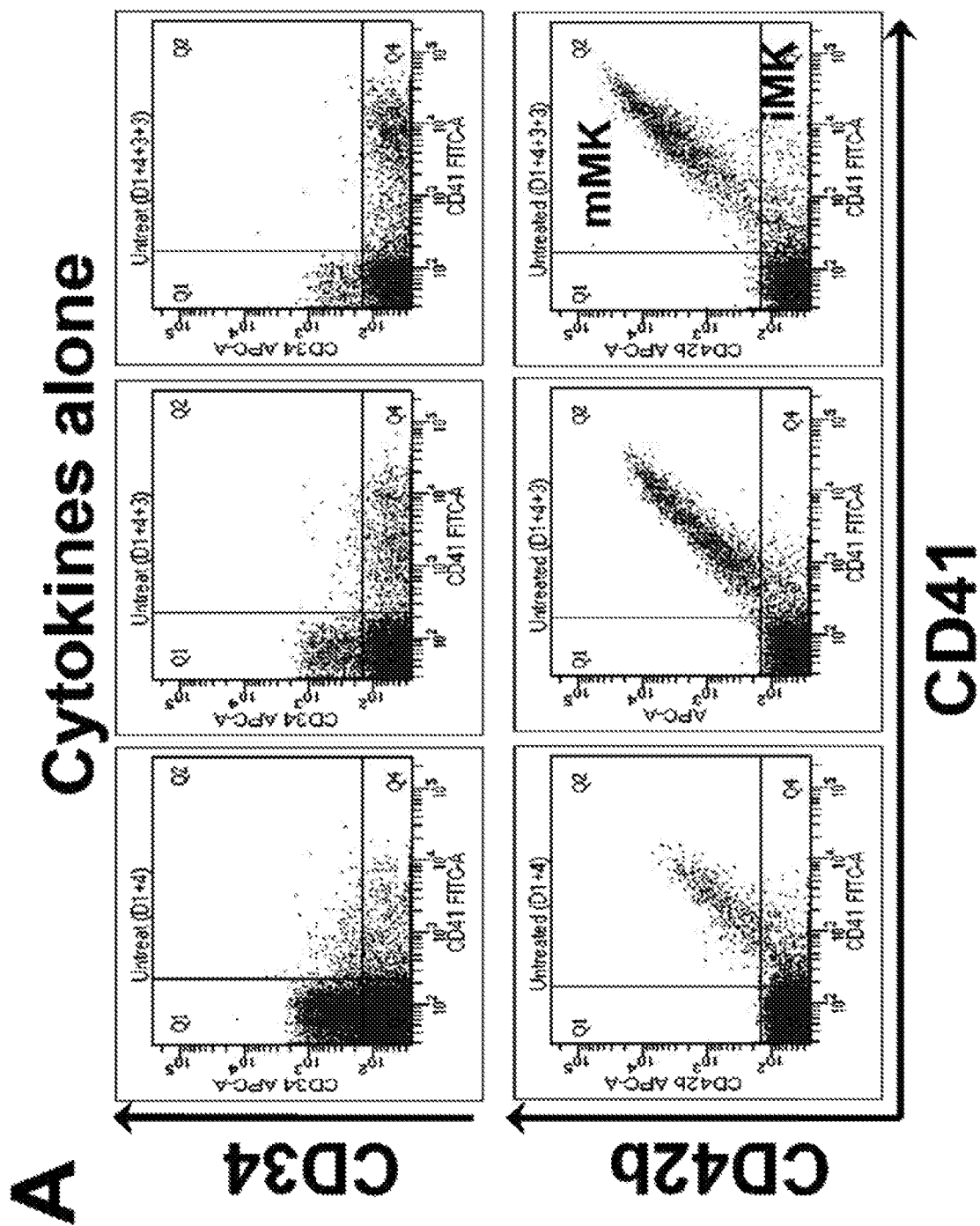
FIGS. 9A and 9B represent flow cytometric analyses of MK cultures expanded in the presence of cytokines alone (FIG. 9A) or cytokines plus VPA (FIG. 9B). MK generated after VPA-mediated HSC expansion show early enrichment in the MKP population which results in superior iMK and mMK yields.
Figure 9:
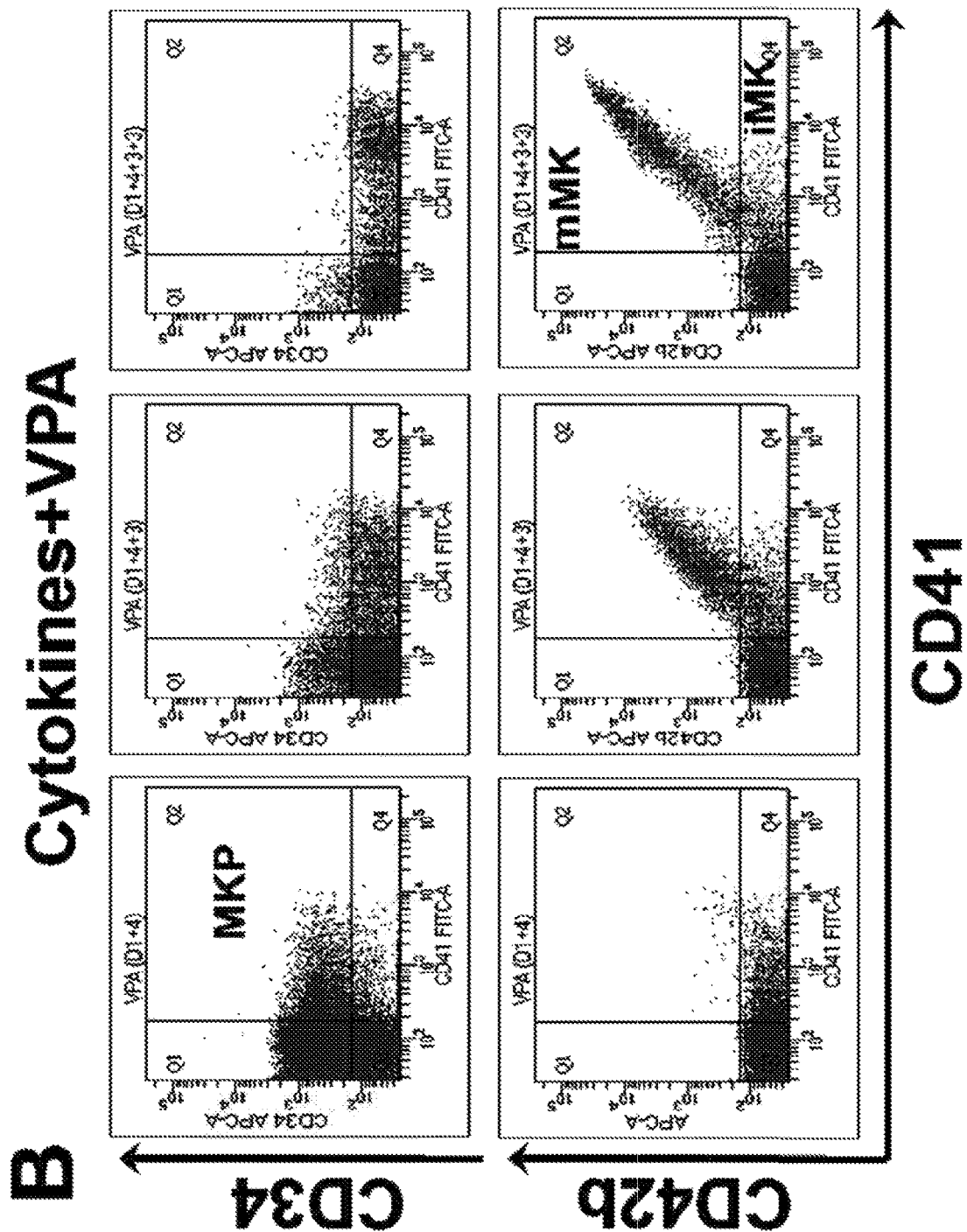
Figure 10:
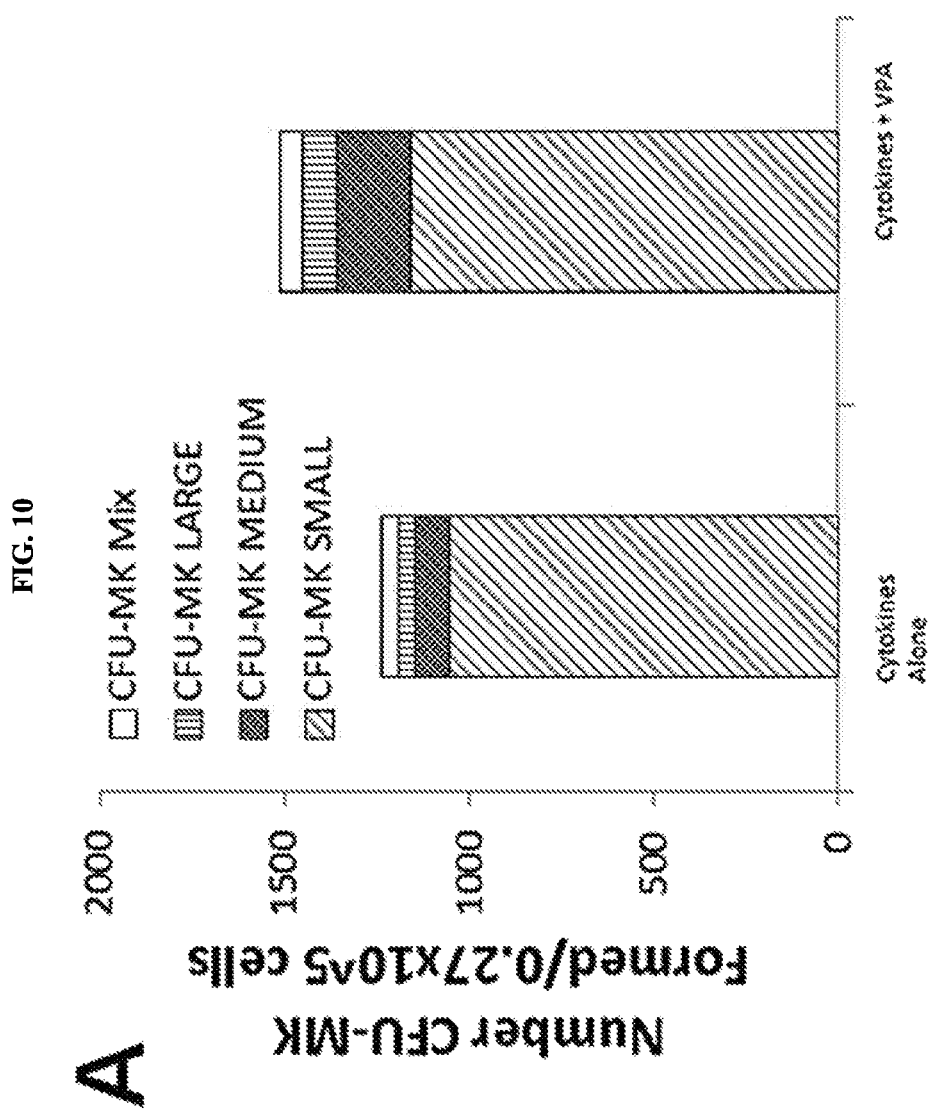
FIGS. 10A and 10B represent MK cultures generated from CD34$^+$ HSC expanded in the presence of cytokines alone or cytokines plus VPA for 7 days: 4 days expansion followed by 3 days MK differentiation, then plated in collagen-based media and allowed to form CFU-MK. The number, and the size (FIG. 10A) as well as morphological appearance (FIG. 10B) of CFU-MKs formed were evaluated after 14 days.
Figure 10:
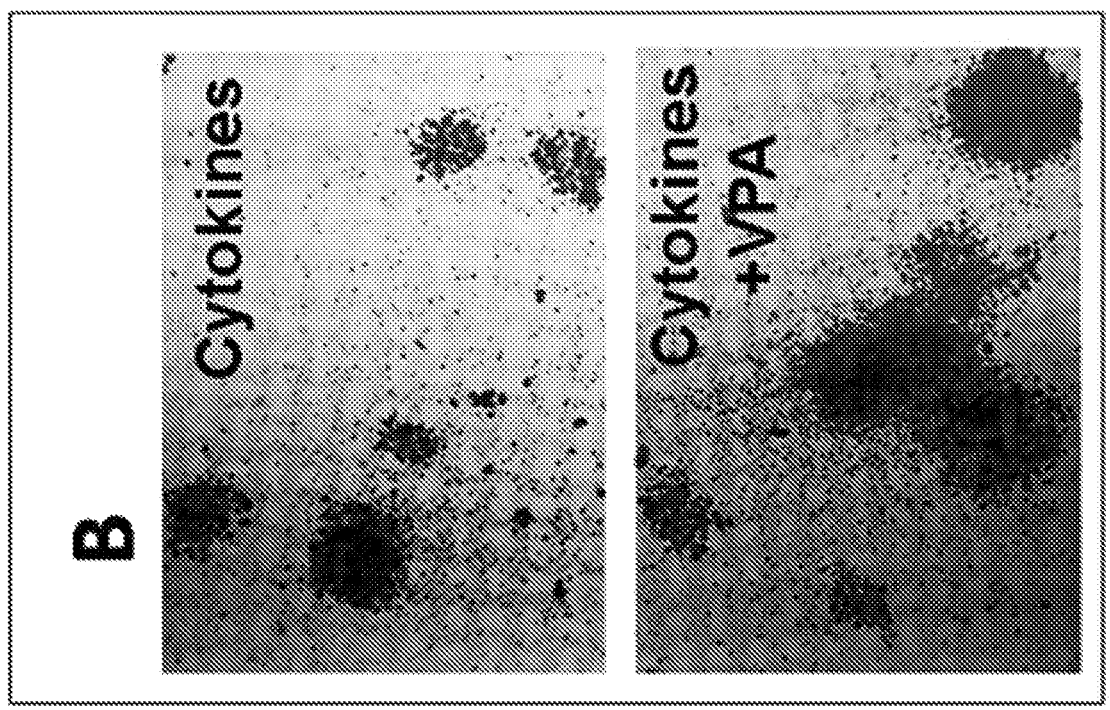

9. Averaged Megakaryocyte Yields from Culture Optimizations and Additional Ex Vivo Characterization of Certain Cell Culture Conditions CD34+ HSCs derived from cord blood (CB) were expanded for 4 or 7 days in the absence or presence of valproic acid (VPA) then induced towards megakaryocyte (MK) differentiation and maturation in conditions employing various cytokine cocktails. The cell culture conditions without VPA ("cytokines alone") include CC #1-4, 9-14 as described herein, and those with VPA ("cytokines+VPA") include CC #5-8, 15-20 as described herein. The average±standard deviation (SD) of MK yields both groups of cell cultures is represented in TABLE 4 below. Representative flow cytometric analyses are represented in FIGS. 9A (CC #11 for cytokines only) and 9B (CC #17 for cytokines+VPA). Representative number of CFUs taken at a common time point (day 8) for "cytokines alone" as well as for "cytokines+VPA" are represented in FIG. 10.

TABLE 4

MK yields from culture optimization

| Culture Conditions | Absolute number of CD41+ MK per input CD34+ cell plated | Anticipated number of CD41+ MK per input CD34+ cell plated | Fraction of MK in the Expanded Product (%) |
|---|---|---|---|
| Cytokines alone (n = 10, CC#1-4, 9-14) | 19 ± 8.2 | 39.7 ± 16.5 | 14.9 ± 3.9 |
| Cytokines + VPA (n = 10, CC#5-8, 15-20) | 20.7 ± 8.4 | 41.4 ± 16.8 | 27.5 ± 5.8 |

These culture conditions represent optimization to further maximize the fraction of MK yields generated which can vary between 15 to 57% of culture. The predominant subpopulation of MK resulted in these conditions consists of mMKs, regardless of VPA treatment. However, the cultures generated in the presence of VPA contained a greater number of CD34+/CD41+ MK precursors and assayable CFU-MKs as compared to cytokines alone (see FIG. 9).

10. Additional Cell Culture Protocols

The following additional cell culture protocols were performed on cord blood (CB) CD34+ cells.

Treatment 1: (CC #1)
Day 0:
The CB CD34+ cells were primed with a cytokine cocktail and plated in serum-free (SF) culture (Stemline media). The cytokine cocktail included stem cell factor (SCF) at an amount of 150 ng/mL, interleukin-3 (IL-3) at an amount of 50 ng/mL, Fms-like tyrosine kinase 3 (FLT-3) at an amount of 100 ng/mL, and thrombopoietin (TPO) at an amount of 100 ng/mL.

Days 1 Through 8:
The cells were allowed to expand in the SF culture.
Days 8 Through 12:
The cells were re-plated in Stemline media with 150 ng/mL SCF and 100 ng mL TPO.
Day 12:
The cells were collected.

Treatment 2: (CC #2)
Day 0:
The CB CD34+ cells were primed with a cytokine cocktail and plated in serum-free (SF) culture (Stemline media). The cytokine cocktail included stem cell factor (SCF) at an amount of 150 ng/mL, interleukin-3 (IL-3) at an amount of 50 ng/mL, Fms-like tyrosine kinase 3 (FLT-3) at an amount of 100 ng/mL, and thrombopoietin (TPO) at an amount of 100 ng/mL.

Days 1 Through 8:
The cells were allowed to expand in the SF culture.
Days 8 Through 12:
The cells were re-plated in Stemline media with 100 ng mL TPO only.
Day 12:
The cells were collected.

Treatment 3: (CC #3)
Day 0:
The CB CD34+ cells were primed with a cytokine cocktail and plated in serum-free (SF) culture (Stemline media). The cytokine cocktail included stem cell factor (SCF) at an amount of 150 ng/mL, interleukin-3 (IL-3) at an amount of 50 ng/mL, Fms-like tyrosine kinase 3 (FLT-3) at an amount of 100 ng/mL, and thrombopoietin (TPO) at an amount of 100 ng/mL.

Days 1 Through 8:
The cells were allowed to expand in the SF culture.
Days 8 Through 12:
The cells were re-plated in QBSF media with 150 ng/mL SCF and 100 ng mL TPO.
Day 12:
The cells were collected.

Treatment 4: (CC #4)
Day 0:
The CB CD34+ cells were primed with a cytokine cocktail and plated in serum-free (SF) culture (Stemline media). The cytokine cocktail included stem cell factor (SCF) at an amount of 150 ng/mL, interleukin-3 (IL-3) at an amount of 50 ng/mL, Fms-like tyrosine kinase 3 (FLT-3) at an amount of 100 ng/mL, and thrombopoietin (TPO) at an amount of 100 ng/mL.

Days 1 Through 8:
The cells were allowed to expand in the SF culture.
Days 8 Through 12:
The cells were re-plated in QBSF media with 100 ng mL TPO only.
Day 12:
The cells were collected.
Treatment 5: (CC #5)
Day 0:
The CB CD34+ cells were primed with a cytokine cocktail and plated in serum-free (SF) culture (Stemline media). The cytokine cocktail included stem cell factor (SCF) at an amount of 150 ng/mL, interleukin-3 (IL-3) at an amount of 50 ng/mL, Fms-like tyrosine kinase 3 (FLT-3) at an amount of 100 ng/mL, and thrombopoietin (TPO) at an amount of 100 ng/mL.
Day 1:
1 mM valproic acid (VPA) was added to the SF culture.
Days 1 Through 8:
The cells were allowed to expand in the SF culture.
Days 8 Through 12:
The cells were re-plated in Stemline media with 150 ng/mL SCF and 100 ng/mL TPO.
Day 12:
The cells were collected.
Treatment 6: (CC #6)
Day 0:
The CB CD34+ cells were primed with a cytokine cocktail and plated in serum-free (SF) culture (Stemline media). The cytokine cocktail included stem cell factor (SCF) at an amount of 150 ng/mL, interleukin-3 (IL-3) at an amount of 50 ng/mL, Fms-like tyrosine kinase 3 (FLT-3) at an amount of 100 ng/mL, and thrombopoietin (TPO) at an amount of 100 ng/mL.
Day 1:
1 mM valproic acid (VPA) was added to the SF culture.
Days 1 Through 8:
The cells were allowed to expand in the SF culture.
Days 8 Through 12:
The cells were re-plated in Stemline media with 100 ng/mL TPO only.
Day 12:
The cells were collected.
Treatment 7: (CC #7)
Day 0:
The CB CD34+ cells were primed with a cytokine cocktail and plated in serum-free (SF) culture (Stemline media). The cytokine cocktail included stem cell factor (SCF) at an amount of 150 ng/mL, interleukin-3 (IL-3) at an amount of 50 ng/mL, Fms-like tyrosine kinase 3 (FLT-3) at an amount of 100 ng/mL, and thrombopoietin (TPO) at an amount of 100 ng/mL.
Day 1:
1 mM valproic acid (VPA) was added to the SF culture.
Days 1 Through 8:
The cells were allowed to expand in the SF culture.
Days 8 Through 12:
The cells were re-plated in QBSF media with 150 ng/mL SCF and 100 ng/mL TPO.
Day 12:
The cells were collected.
Treatment 8: (CC #8)
Day 0:
The CB CD34+ cells were primed with a cytokine cocktail and plated in serum-free (SF) culture (Stemline media). The cytokine cocktail included stem cell factor (SCF) at an amount of 150 ng/mL, interleukin-3 (IL-3) at an amount of 50 ng/mL, Fms-like tyrosine kinase 3 (FLT-3) at an amount of 100 ng/mL, and thrombopoietin (TPO) at an amount of 100 ng/mL.
Day 1:
1 mM valproic acid (VPA) was added to the SF culture.
Days 1 Through 8:
The cells were allowed to expand in the SF culture.
Days 8 Through 12:
The cells were re-plated in QBSF media with 100 ng/mL TPO only.
Day 12:
The cells were collected.
Treatment 9: (CC #9)
Days 0 Through 5:
The CB CD34+ cells were primed with a cytokine cocktail and plated in serum-free (SF) culture (Stemline media). The cytokine cocktail included stem cell factor (SCF) at an amount of 150 ng/mL, interleukin-3 (IL-3) at an amount of 50 ng/mL, Fms-like tyrosine kinase 3 (FLT-3) at an amount of 100 ng/mL, and thrombopoietin (TPO) at an amount of 100 ng/mL. The cells were allowed to expand in the SF culture.
Days 5-12:
The cells were re-plated in Stemline media with 150 ng/mL SCF and 100 ng/mL TPO.
Day 12:
The cells were collected.
Treatment 10: (CC #10)
Days 0 Through 5:
The CB CD34+ cells were primed with a cytokine cocktail and plated in serum-free (SF) culture (Stemline media). The cytokine cocktail included stem cell factor (SCF) at an amount of 150 ng/mL, interleukin-3 (IL-3) at an amount of 50 ng/mL, Fms-like tyrosine kinase 3 (FLT-3) at an amount of 100 ng/mL, and thrombopoietin (TPO) at an amount of 100 ng/mL. The cells were allowed to expand in the SF culture.
Days 5-8:
The cells were re-plated in Stemline media with 150 ng/mL SCF and 100 ng/mL TPO. The cells were allowed to expand.
Days 8-12:
The cells were re-plated in ½ volume Stemline media with 150 ng/mL SCF and 100 ng/mL TPO.
Day 12:
The cells were collected.
Treatment 11: (CC #12)
Days 0 Through 5:
The CB CD34+ cells were primed with a cytokine cocktail and plated in serum-free (SF) culture (Stemline media). The cytokine cocktail included stem cell factor (SCF) at an amount of 150 ng/mL, interleukin-3 (IL-3) at an amount of 50 ng/mL, Fms-like tyrosine kinase 3 (FLT-3) at an amount of 100 ng/mL, and thrombopoietin (TPO) at an amount of 100 ng/mL. The cells were allowed to expand in the SF culture.
Days 5-12:
The cells were re-plated in Stemline media with 10 ng/mL SCF and 100 ng/mL TPO.
Day 12:
The cells were collected.
Treatment 12: (CC #13)
Days 0 Through 5:
The CB CD34+ cells were primed with a cytokine cocktail and plated in serum-free (SF) culture (Stemline media). The cytokine cocktail included stem cell factor (SCF) at an amount of 150 ng/mL, interleukin-3 (IL-3) at an amount of 50 ng/mL, Fms-like tyrosine kinase 3 (FLT-3) at an amount of 100 ng/mL, and thrombopoietin (TPO) at an amount of 100 ng/mL. The cells were allowed to expand in the SF culture.

Days 5 Through 8:
The cells were re-plated in Stemline media with 10 ng/mL SCF and 100 ng/mL TPO. The cells were allowed to expand.

Days 8 Through 12:
The cells were re-plated in ½ volume Stemline media with 150 ng/mL SCF and 100 ng/mL TPO.

Day 12:
The cells were collected.

Treatment 13: (CC #16)

Day 0:
The CB CD34+ cells were primed with a cytokine cocktail and plated in serum-free (SF) culture (Stemline media). The cytokine cocktail included stem cell factor (SCF) at an amount of 150 ng/mL, interleukin-3 (IL-3) at an amount of 50 ng/mL, Fms-like tyrosine kinase 3 (FLT-3) at an amount of 100 ng/mL, and thrombopoietin (TPO) at an amount of 100 ng/mL.

Day 1:
1 mM valproic acid (VPA) was added to the SF culture.

Days 1 Through 5:
The cells were allowed to expand in the SF culture.

Day 5:
The cells were re-plated in Stemline media with 150 ng/mL SCF and 100 ng/mL TPO.

Days 5 Through 8:
The cells were allowed to expand in the SF culture.

Day 8:
The cells were re-plated in ½ volume Stemline media with 150 ng/mL SCF and 100 ng/mL TPO.

Days 8 Through 12:
The cells were allowed to expand in the SF culture.

Day 12:
The cells were collected.

Treatment 14: (CC #18)

Day 0:
The CB CD34+ cells were primed with a cytokine cocktail and plated in serum-free (SF) culture (Stemline media). The cytokine cocktail included stem cell factor (SCF) at an amount of 150 ng/mL, interleukin-3 (IL-3) at an amount of 50 ng/mL, Fms-like tyrosine kinase 3 (FLT-3) at an amount of 100 ng/mL, and thrombopoietin (TPO) at an amount of 100 ng/mL. Day 1:
1 mM valproic acid (VPA) was added to the SF culture.

Days 1 Through 5:
The cells were allowed to expand in the SF culture.

Day 5:
The cells were re-plated in Stemline media with 10 ng/mL SCF and 100 ng/mL TPO.

Days 5 Through 12:
The cells were allowed to expand in the SF culture.

Day 12:
The cells were collected.

Treatment 15: (CC #20)

Day 0:
The CB CD34+ cells were primed with a cytokine cocktail and plated in serum-free (SF) culture (Stemline media). The cytokine cocktail included stem cell factor (SCF) at an amount of 150 ng/mL, interleukin-3 (IL-3) at an amount of 50 ng/mL, Fms-like tyrosine kinase 3 (FLT-3) at an amount of 100 ng/mL, and thrombopoietin (TPO) at an amount of 100 ng/mL.

Day 1:
1 mM valproic acid (VPA) was added to the SF culture.

Days 1 Through 5:
The cells were allowed to expand in the SF culture.

Day 5:
The cells were re-plated in Stemline media with 10 ng/mL SCF and 100 ng/mL TPO.

Days 5 Through 8:
The cells were allowed to expand in the SF culture.

Day 8:
The cells were re-plated in Stemline media with 100 ng/mL TPO only.

Days 8 Through 12:
The cells were allowed to expand in the SF culture.

Day 12:
The cells were collected.

TABLE 5

CD41+ Megakaryocyte yield, actual vs. theoretical, organized by culture conditions labeled in the Examples.

| | Absolute number of CD41+ MK generated | |
|---|---|---|
| Culture Conditions | Per one CD34+ cell plated | Anticipated per one CBU of $2 \times 10^6$ CD34+ cells |
| CC#1 | 29.2 ± 16 | $58.4 \times 10^6$ |
| CC#2 | 18.1 ± 8 | $36.2 \times 10^6$ |
| CC#3 | 32.7 ± 13 | $65.4 \times 10^6$ |
| CC#4 | 22.1 ± 10 | $44.2 \times 10^6$ |
| CC#5 | 9.9 ± 2 | $16 \times 10^6$ |
| CC#6 | 22.3 ± 11 | $48.8 \times 10^6$ |
| CC#7 | 11.7 ± 10 | $31.6 \times 10^6$ |
| CC#8 | 27.8 ± 9 | $16 \times 10^6$ |
| CC#9 | 24.3 ± 13 | $48.8 \times 10^6$ |
| CC#10 | 24.4 | $31.6 \times 10^6$ |
| CC#11 | 15.8 | $19.8 \times 10^6$ |
| CC#12 | 8 | $44.6 \times 10^6$ |
| CC#13 | 24.4 | $23.4 \times 10^6$ |
| CC#14 | 15.8 | $55.6 \times 10^6$ |
| CC#15 | 22 | $44 \times 10^6$ |
| CC#16 | 29.8 | $59.6 \times 10^6$ |
| CC#17 | 13.4 | $26.8 \times 10^6$ |
| CC#18 | 23.6 | $47.2 \times 10^6$ |
| CC#19 | 34.0 | $68 \times 10^6$ |
| CC#20 | 12.7 | $25.4 \times 10^6$ |

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

The invention claimed is:

1. A method of obtaining mature CD41$^+$ megakaryocytes, the method comprising:
   (i) culturing an isolated population of cells comprising CD34$^+$ hematopoietic stem cells (HSCs) in a first media, wherein the first media is serum-free and comprises stem cell factor (SCF) in an amount from about 1 ng/mL to about 250 ng/mL, interleukin-3 (IL-3) in an amount from about 1 ng/mL to about 100 ng/mL, thrombopoietin (TPO) in an amount from about 1 ng/mL to about 200 ng/mL, and Fms-like tyrosine kinase 3 (FLT-3) in an amount from about 1 ng/mL to about 200 ng/mL, and expanding the cells a first time for no more than 24 hours;
(ii) culturing the cells obtained by step (i) in a second media, wherein the second media is serum-free and comprises SCF in an amount from about 1 ng/mL to about 250 ng/mL, IL-3 in an amount from about 1 ng/mL to about 100 ng/mL, TPO in an amount from about 1 ng/mL to about 200 ng/mL, FLT-3 in an amount from about 1 ng/mL to about 200 ng/mL, and valproic acid (VPA) in an amount from about 0.1 mM to about 5 mM, and expanding the cells for about 96 hours;
(iii) culturing the cells obtained by step (ii) in a third media, wherein the third media is serum-free and comprises SCF in an amount from about 1 ng/mL to about 250 ng/mL and TPO in an amount from about 1 ng/mL to about 250 ng/mL, and expanding the cells for about 72 hours;
(iv) culturing the cells obtained by step (iii) in a fourth media, wherein the fourth media is serum-free and comprises SCF from about 10 ng/ml to about 150 ng/ml and TPO in an amount from about 1 ng/mL to about 200 ng/mL, and culturing the cells in the fourth media for about 96 hours; and
(v) collecting the resultant megakaryocytes.

2. The method of claim 1, wherein the population of cells comprising hematopoietic stem cells are isolated from cord blood (CB), bone marrow (BM), peripheral blood (PB), or combinations thereof.

3. The method of claim 1, wherein the first or the second media further comprises interleukin-6 (IL-6).

4. The method of claim 1, wherein the megakaryocytes comprise at least one of megakaryocyte progenitors, immature megakaryocytes, mature megakaryocytes, and combinations thereof.

5. The method of claim 1, wherein the first media comprises:
   (a) SCF in an amount of about 150 ng/mL;
   (b) IL-3 in an amount of about 50 ng/mL;
   (c) TPO in an amount of about 100 ng/mL; and
   (d) FLT-3 in an amount of 100 ng/mL.

6. The method of claim 1, wherein the second media comprises:
   (a) SCF in an amount of about 150 ng/mL;
   (b) IL-3 in an amount of about 50 ng/mL;
   (c) TPO in an amount of about 100 ng/mL; and
   (d) FLT-3 in an amount of 100 ng/mL.

7. The method of claim 1, wherein the second media comprises VPA in an amount of about 1 mM.

8. The method of claim 1, wherein the third media comprises:
   (a) SCF in an amount of about 10 ng/mL or about 150 ng/mL; and
   (b) TPO in an amount of about 100 ng/mL.

9. The method of claim 1, wherein the fourth media comprises:
   (a) SCF in an amount of about 10 ng/mL or about 150 ng/mL; and
   (b) TPO in an amount of about 100 ng/mL.

10. A method of obtaining mature CD41+ megakaryocytes, the method comprising:
(i) culturing an isolated population of cells comprising CD34+ HSCs in a first media, wherein the first media is serum-free and comprises SCF in an amount of about 150 ng/mL, IL-3 in an amount of about 50 ng/mL, TPO in an amount of about 100 ng/mL, and FLT-3 in an amount of 100 ng/mL, and expanding the cells a first time for about 24 hours;
(ii) culturing the cells obtained by step (i) in a second media, wherein the second media is serum-free and comprises SCF in an amount from about 1 ng/mL to about 250 ng/mL, IL-3 in an amount from about 1 ng/mL to about 100 ng/mL, TPO in an amount from about 1 ng/mL to about 200 ng/mL, FLT-3 in an amount from about 1 ng/mL to about 200 ng/mL, and VPA in an amount from about 0.1 mM to about 5 mM, and expanding the cells for about 96 hours;
(iii) culturing the cells obtained by step (ii) in a third media, wherein the third media is serum-free and comprises SCF in an amount from about 1 ng/mL to about 250 ng/mL and TPO in an amount from about 1 ng/mL to about 250 ng/mL, and expanding the cells for about 72 hours;
(iv) culturing the cells obtained by step (iii) in a fourth media, wherein the fourth media is serum-free and comprises SCF from about 10 ng/ml to about 150 ng/ml and TPO in an amount from about 1 ng/mL to about 200 ng/mL, and culturing the cells in the fourth media for about 96 hours; and
(v) collecting the resultant megakaryocytes.

11. The method of claim 10, wherein the second media comprises:
   (a) SCF in an amount of about 150 ng/mL;
   (b) IL-3 in an amount of about 50 ng/mL;
   (c) TPO in an amount of about 100 ng/mL; and
   (d) FLT-3 in an amount of 100 ng/mL.

12. The method of claim 10, wherein the second media comprises VPA in an amount of about 1 mM.

13. The method of claim 10, wherein the third media comprises:
   (a) SCF in an amount of about 10 ng/mL or about 150 ng/mL; and
   (b) TPO in an amount of about 100 ng/mL.

14. The method of claim 10, wherein the fourth media comprises:
   (a) SCF in an amount of about 10 ng/mL or about 150 ng/mL; and
   (b) TPO in an amount of about 100 ng/mL.

15. A method of obtaining mature CD41+ megakaryocytes, the method comprising:
(i) culturing an isolated population of cells comprising CD34+ HSCs in a first media, wherein the first media is serum-free and SCF in an amount from about 1 ng/mL to about 250 ng/mL, IL-3 in an amount from about 1 ng/mL to about 100 ng/mL, TPO in an amount from about 1 ng/mL to about 200 ng/mL, and FLT-3 in an amount from about 1 ng/mL to about 200 ng/mL, and expanding the cells a first time for about 24 hours;
(ii) culturing the cells obtained by step (i) in a second media wherein the second media comprises SCF in an amount of about 150 ng/mL, IL-3 in an amount of about 50 ng/mL, TPO in an amount of about 100 ng/mL, FLT-3 in an amount of about 100 ng/mL, and VPA in an amount from about 0.1 mM to about 5 mM, and expanding the cells for about 96 hours;
(iii) culturing the cells obtained by step (ii) in a third media, wherein the third media is serum-free and comprises SCF in an amount from about 1 ng/mL to about 250 ng/mL and TPO in an amount from about 1 ng/mL to about 250 ng/mL, and expanding the cells for about 72 hours;
(iv) culturing the cells obtained by step (iii) in a fourth media, wherein the fourth media is serum-free and comprises SCF from about 10 ng/ml to about 150 ng/ml and TPO in an amount from about 1 ng/mL to about 200 ng/mL, and culturing the cells in the fourth media for about 96 hours; and (v) collecting the resultant megakaryocytes.

16. The method of claim 15, wherein the first media comprises:

(a) SCF in an amount of about 150 ng/mL;
(b) IL-3 in an amount of about 50 ng/mL;
(c) TPO in an amount of about 100 ng/mL; and
(d) FLT-3 in an amount of 100 ng/mL.

17. The method of claim 15, wherein the second media comprises VPA in an amount of about 1 mM.

18. The method of claim 15, wherein the third media comprises:

(a) SCF in an amount of about 10 ng/mL or about 150 ng/mL; and
(b) TPO in an amount of about 100 ng/mL.

19. The method of claim 15, wherein the fourth media comprises:

(a) SCF in an amount of about 10 ng/mL or about 150 ng/mL; and
(b) TPO in an amount of about 100 ng/mL.

20. The method of claim 1, wherein the expansion step (ii) is for no more than 96 hours.

\* \* \* \* \*